US012624239B2

(12) United States Patent
Abidian et al.

(10) Patent No.: US 12,624,239 B2
(45) Date of Patent: May 12, 2026

(54) HIGHLY CONDUCTIVE AND BIOACTIVE PHOTOSENSITIVE RESINS FOR DEVELOPMENT OF FUNCTIONAL AND HYBRID ELECTRONICS AND SENSORS

(71) Applicant: University of Houston System, Houston, TX (US)

(72) Inventors: Mohammad Reza Abidian, Houston, TX (US); Omid Dadras-Toussi, Houston, TX (US); Milad Khorrami, Hayward, CA (US); Sheereen Majd, Houston, TX (US)

(73) Assignee: UNIVERSITY OF HOUSTON SYSTEM, Houston, TX (US)

( * ) Notice: Subject to any disclaimer, the term of this patent is extended or adjusted under 35 U.S.C. 154(b) by 712 days.

(21) Appl. No.: 17/932,889

(22) Filed: Sep. 16, 2022

(65) Prior Publication Data

US 2023/0088763 A1     Mar. 23, 2023

Related U.S. Application Data

(60) Provisional application No. 63/245,321, filed on Sep. 17, 2021.

(51) Int. Cl.
*C09D 11/52*        (2014.01)
*G01N 33/543*        (2006.01)
(52) U.S. Cl.
CPC ....... *C09D 11/52* (2013.01); *G01N 33/54373* (2013.01)
(58) Field of Classification Search
None
See application file for complete search history.

(56) References Cited

U.S. PATENT DOCUMENTS

| | | | | |
|---|---|---|---|---|
| 7,579,386 B1 * | 8/2009 | Matroni | ............. | C08G 59/1494 |
| | | | | 522/182 |
| 2007/0176152 A1 | 8/2007 | Xing-Fu | | |

(Continued)

FOREIGN PATENT DOCUMENTS

| | | |
|---|---|---|
| CN | 113174166 | 7/2021 |
| JP | 2009-155570 | 7/2009 |

OTHER PUBLICATIONS 3D fabrication of all-polymer conductive microstructures by two photon polymerization, Kurselis et al., Optics Express, Dec. 9, 2013, vol. 21, No. 25 (Year: 2013).*

(Continued)

*Primary Examiner* — Peter A Salamon
(74) *Attorney, Agent, or Firm* — pH IP Law

(57)        ABSTRACT

The present disclosure describes a new resin which can be fabricated into conductive and bioactive microstructures via two-photon polymerization. The direct incorporation of conductive poly (3,4-ethylenedioxythiophene)-poly(styrenesulfonate) (PEDOT:PSS) and/or multi-walled carbon nanotubes (MWCNTs) in a poly(ethylene glycol) diacrylate (PEGDA)-based blend remarkably enhances the electrical conductivity of microstructures over 10 orders of magnitude. Including biomaterials in the resin can promote cellular adhesion and create functional biosensors made of hybrid non-conductive and conductive structures for sensitive detection. Applications include development cost effective microelectronics in a broad range of biomedical research, electronics and sensors.

19 Claims, 23 Drawing Sheets
(22 of 23 Drawing Sheet(s) Filed in Color)

(56) References Cited

U.S. PATENT DOCUMENTS

| | | | |
|---|---|---|---|
| 2012/0128882 A1 | 5/2012 | Mirkin et al. | |
| 2012/0186470 A1* | 7/2012 | Marco | B41M 7/0081 |
| | | | 101/483 |
| 2014/0151607 A1* | 6/2014 | Lowenthal | C09D 11/101 |
| | | | 252/514 |
| 2020/0401042 A1 | 12/2020 | Bao et al. | |

OTHER PUBLICATIONS

Simultaneoulsy Enhancing the Cohesion and Electrical Conductivity of PEDOT:PSS Conductive Polymer Films using DMSO Additives, Lee et al., Applied Materials and Interfaces, 2016, 8, 302-310 (Year: 2016).*
EDOT polymerization Google scholar search (Year: 2025).*
Abidian & Martin, "Experimental and theoretical characterization of implantable neural microelectrodes modified with conducting polymer nanotubes," *Biomaterials*, vol. 29, No. 9, pp. 1273-1283, 2008.
Abidian & Martin, "Multifunctional nanobiomaterials for neural interfaces," *Advanced Functional Materials*, vol. 19, No. 4, pp. 573-585, 2009.
Abidian et al., "Conducting-polymer nanotubes for controlled drug release," *Advanced Materials*, vol. 18, No. 4, pp. 405-409, 2006.
Abidian et al., "Conducting-polymer nanotubes improve electrical properties, mechanical adhesion, neural attachment, and neurite outgrowth of neural electrodes," *Nano-Micro Small*, vol. 6, No. 3, pp. 421-429, 2010.
Abidian et al., "Interfacing conducting polymer nanotubes with the central nervous system: chronic neural recording using poly (3, 4-ethylenedioxythiophene) nanotubes," *Advanced Materials*, vol. 21, No. 37, pp. 3764-3770, 2009.
Agarwala et al., "Development of bendable strain sensor with embedded microchannels using 3D printing," *Sensors and Actuators A: Physical*, vol. 263, pp. 593-599, 2017.
Antensteiner et al., "Conducting polymer microcups for organic bioelectronics and drug delivery applications," *Adv. Mater.* vol. 29, No. 39, p. 1702576, 2017.
Arica et al., "Immobilization of glucose oxidase: a comparison of entrapment and covalent bonding," *J. Chemical Technology & Biotechnology*, vol. 58, No. 3, pp. 287-292, 1993.
Chen, Yan-Shi, Jin-Hua Huang, and Chia-Chih Chuang. "Glucose biosensor based on multiwalled carbon nanotubes grown directly on Si." *Carbon* 47.13 (2009): 3106-3112.
Christwardana et al., ,,Highly sensitive glucose biosensor using new glucose oxidase based biocatalyst, *Korean J. Chem. Eng.* 2017, 34, 2916.
Da Violante et al., "Evaluation of the cytotoxicity effect of dimethyl sulfoxide (DMSO) on Caco2/TC7 colon tumor cell cultures," *Biol Pharm Bull*, vol. 25, No. 12, pp. 1600-1603, 2002.
Dadras-Toussi et al., "Direct Laser 3D Printing of Organic Semiconductor Microdevices for Bioelectronics and Biosensors", *2022 44th Annual International Conference of the IEEE Engineering in Medicine & Biology Society (EMBC)*, *IEEE*, pp. 1569-1572, Jul. 11, 2022.
Dadras-Toussi et al., "Femtosecond Laser 3D-printing of Conductive Microelectronics for Potential Biomedical Applications", *2021 43th Annual International Conference of the IEEE Engineering in Medicine & Biology Society (EMBC)*, IEEE, pp. 1197-1200, Oct. 2021.
Dadras-Toussi et al., Multiphoton Lighography of Organic Semiconductor Devices for 3D Printing of Flexible Electronci Circuits, Biosensors, and Bioelectronics, *Advanced Materials*, 2200512, p. 1-14, Jul. 2022.
De Fazio et al., "Alterations in cerebral oxidative metabolism following traumatic brain injury," *Neurocritical Care*, vol. 14, No. 1, pp. 91-96, 2011.

Dong & Portale, "Role of the Processing Solvent on the Electrical Conductivity of Pedot: PSS," *Advanced Materials*, vol. 7, No. 18, p. 2000641, 2020.
Giannelli et al., "Induction of cell migration by matrix metalloprotease-2 cleavage of laminin-5," *Science*, vol. 277, No. 5323, pp. 225-228, 1997.
Guimard et al., "Conducting polymers in biomedical engineering," *Progress in Polymer Science*, vol. 32, No. 8-9, pp. 876-921, 2007.
Guo et al., "Using laser microfabrication to write conductive polymer/SWNTs nanocomposites", 7(1):44, 2012.
Gürsel & Hasirci, "Matrix entrapment of glucose oxidase by γ irradiation," Biomaterials, vol. 13, No. 3, pp. 150-155, 1992.
Heo et al., "Development of 3D printable conductive hydrogel with crystallized PEDOT:PSS for neural tissue engineering", *Materials Science & Engineering C*, 99:582-590, 2019.
International Preliminary Report on Patentability for PCT/US2022/076531 dated Nov. 28, 2023, 20 pages.
International Search Report and Written Opinion for PCT/US2022/076531 dated Jan. 1, 2023, 18 pages.
International Second Written Opinion for PCT/US2022/076531 dated Aug. 3, 2023, 8 pages.
Jung et al., ,,Improved Sensitivity of a Glucose Sensor by Encapsulation of Free Gox in Conducting Polymer Micropillar Structure, *J. Electrochem. Sci. Technol*, 2(2), 124-129, 2011.
Kandel et al., "Principles of neural science", *McGraw-hill New York*, 2021. Chapter 39.
Kawata et al., "Finer features for functional microdevices," *Nature*, vol. 412, No. 6848, pp. 697-698, 2001.
Khorrami A Dissertation Presented to the Faculty of the Department of Biomedical Engineering, University of Houston, In Partial Fulfillment of the Requirements for the Degree Doctor of Philosophy in Biomedical Engineering, May 2019.
Kros et al.,"Poly (3, 4-ethylenedioxythiophene)-based glucose biosensors," *Adv. Mater* vol. 13, No. 20, pp. 1555-1557, 2001.
Kurselis et al., "3D fabrication of all-polymer conductive microstructures by two photon polymerization", 21(25):31029-31035, 2013.
Li et al., "Achieving λ/20 resolution by one-color initiation and deactivation of polymerization," *Science*, vol. 324, No. 5929, pp. 910-913, 2009.
Li et al., "Biocomposites of covalently linked glucose oxidase on carbon nanotubes for glucose biosensor", *Anal. Bioanal. Chem.* 2005, 383, 918.
Liu et al., "Amperometric glucose biosensor based on single-walled carbon nanohorns", *Biosens. Bioelectron.* 2008, 23, 1887.
Long et al., "Recent advances in synthesis, physical properties and applications of conducting polymer nanotubes and nanofibers," *Progress in Polymer Science*, vol. 36, No. 10, pp. 1415-1442, 2011.
Ludwig et al., "Chronic neural recordings using silicon microelectrode arrays electrochemically deposited with a poly (3, 4-ethylenedioxythiophene)(PEDOT) film," *Journal of Neural Engineering*, vol. 3, No. 1, p. 59, 2006.
Macaya et al., "Simple glucose sensors with micromolar sensitivity based on organic electrochemical transistors," *Sens. Actuat. B-Chem.* vol. 123, No. 1, pp. 374-378, 2007.
Malliaras & Abidian, "Organic bioelectronic materials and devices," vol. 27, No. 46, p. 7492, 2015.
McCarthy et al., "The role of cell adhesion proteins—laminin and fibronectin—in the movement of malignant and metastatic cells," *Cancer Metast Rev*, vol. 4, No. 2, pp. 125-152, 1985.
Nguyen et al., "Facile fabrication of flexible glutamate biosensor using direct writing of platinum nanoparticle-based nanocomposite ink", *Biosensors and Bioelectroncis*, 131, pp. 257-266, Jan. 31, 2019.
Nien et al., "Amperometric glucose biosensor based on entrapment of glucose oxidase in a poly (3, 4-ethylenedioxythiophene) film," *Electroanalysis*, vol. 18, No. 13-14, pp. 1408-1415, 2006.
Niesler & Hermatschweiler, "Two-Photon Polymerization—A Versatile Microfabrication Tool: From maskless lithography to 3D printing," *Laser Technik Journal*, vol. 12, No. 3, pp. 44-47, 2015.
Oubaha et al., "Graphene-doped photo-patternable ionogels: tuning of conductivity and mechanical stability of 3D microstructures,", *Journal of Materials Chemistry*, 22(21):10552-10559, 2012.

(56)          References Cited

OTHER PUBLICATIONS

Ouyang et al., "High-conductivity poly (3, 4-ethylenedioxythiophene): poly (styrene sulfonate) film and its application in polymer optoelectronic devices," *Advanced Functional Materials*, vol. 15, No. 2, pp. 203-208, 2005.

Piro et al., "A glucose biosensor based on modified-enzyme incorporated within electropolymerised poly (3, 4-ethylenedioxythiophene)(PEDT) films," *J. Electroanal. Chem.* vol. 512, No. 1-2, pp. 101-109, 2001.

Qu et al., "Stiffness, strength and adhesion characterization of electrochemically deposited conjugated polymer films," *Acta Biomaterialia*, vol. 31, pp. 114-121, 2016.

Rajabasadi, Fatemeh, et al. "3D and 4D lithography of untethered microrobots." *Progress in Materials Science, Pergamon Press, GB*, 120:XP086653669, Apr. 16, 2021.

Sakellari et al., "Diffusion-assisted high-resolution direct femtosecond laser writing," ACSNANO, vol. 6, No. 3, pp. 2302-2311, 2012.

Scordo, "A novel highly electrically conductive composite resin for stereolithography", ScuDo poster, Scuolo di Dottoroto—Doctoral School, XXXIII Cycle, 2020.

Senel & Nergiz, "Novel amperometric glucose biosensor based on covalent immobilization of glucose oxidase on poly(pyrrole propylic acid)/Au nanocomposite", *Curr. Appl. Phys.* 2012, 12, 1118.

Setti et al., "An amperometric glucose biosensor prototype fabricated by thermal inkjet printing", *Biosens. Bioelectron.* 2005, 20, 2019.

Spangenberg et al., "Recent advances in two-photon stereolithography," *Updates in Advanced Lithography*, pp. 35-63, 2013.

Staudinger et al. "Development of electrically conductive microstructures based on polymer/CNT nanocomposites vi two-photon polymerization," *Microelectronic Engineering*, 179: 48-55, 2017.

Sun et al., "Controlled multilayer films of sulfonate-capped gold nanoparticles/thionine used for construction of a reagentless bienzymatic glucose biosensor", *Electrochim. Acta*, 2007, 52, 7352.

Tang et al., "Amperometric glucose biosensor based on adsorption of glucose oxidase at platinum nanoparticle-modified carbon nanotube electrode", *Anal. Biochem.* 2004, 331, 89.

Tao et al., "Carbon nanotube-doped electric hydrogels via ultrafast laser processing and loading conductive polymer", *14th National Conference on Laser Technology and Optoelectronics*, 11170, p. 111703U:*International Society for Optics and Photonics*, 2019.

Tao et al., "Nanostructured electrically conductive hydrogels obtained via ultrafast laser processing and self-assembly", 11(18):9176-9184, 2019.

Wu et al., "Fabrication and conductive polyaniline hydrogel using porogen leaching and projection microstereolithography", *Journal of Materials Chemistry*, 3(26):5352-5360, Jan. 1, 2015.

Xiong et al., "Laser-Directed Assembly of Aligned Carbon Nanotubes in Three Dimensions for Multifunctional Device Fabrication", *Advanced Materials, VCH Publishers*, 28(10):2002-2009, 2016.

Xue et al., "In situ immobilization of glucose oxidase in chitosan-gold nanoparticle hybrid film on Prussian Blue modified electode for high-sensitivity glucose detection", *Electrochem. Commun.* 2006, 8, 1468.

Yang et al., "High performance conducting polymer nanofiber biosensors for detection of biomolecules," *Adv. Mater.* vol. 26, No. 29, pp. 4954-4960, 2014.

Yang et al., "Multilayered construction of glucose oxidase and gold nanoparticles on Au electrodes based on layer-by-layer covalent attachment", *Electrochem. Commun.* 2006, 8, 665.

Zhang et al., "Integrating valve-inspired design features into poly (ethylene glycol) hydrogel scaffolds for heart valve tissue engineering," *Acta Biomaterialia*, vol. 14, pp. 11-21, 2015.

Zhang et al., "Covalent attachment of glucose oxidase to an Au electrode modified with gold nanoparticles for use as glucose biosensor" *Bioelectrochemistry* 2005, 67, 15.

Machine translation of JP 2009-155570, downloaded from https://patents.google.com/patent/JP2009155570A/en?oq=JP+2009-155570 on Jan. 11, 2026.

* cited by examiner

HIGHLY CONDUCTIVE AND BIOACTIVE PHOTOSENSITIVE RESINS FOR DEVELOPMENT OF FUNCTIONAL AND HYBRID ELECTRONICS AND SENSORS

PRIORITY CLAIM

This application claims benefit of priority to U.S. Provisional Application Ser. No. 63/245,321 filed Sep. 17, 2021, the entire contents of which are hereby incorporated by reference.

STATEMENT OF FEDERAL GRANT SUPPORT

This invention was made with government support under grant no. R01 NS0872254 awarded by the National Institute of Health. The government has certain rights in the invention.

BACKGROUND

1. Field of the Disclosure

The present disclosure relates generally to the fields of material science, electronics, optics and bioscience. More particular, the disclosure relates to improved materials and methods for the fabrication of electrically conductive micro- and nanostructures with high spatial resolution.

2. Background

Development of new technologies for fabrication of conductive micro/nano structures has become a demanding research topic in various research areas including micro-electronics (Zhao et al., 2013), micro/nano electromechanical systems (Jayne et al., 2018; Bogue, 2013), photonics (Kabessa et al., 2016; Schell et al., 2013), biosensing (Agarwala et al., 2017), and biomedical engineering (Takenaga et al., 2015; Wang et al., 2015). Among numerous fabrication techniques such as stereolithography, digital light processing, and electron beam melting, direct laser writing (DLW) based on two-photon polymerization (TPP) stands out since it utilizes femtosecond laser beams to create three dimensional (3D) structures with complex shapes in sub-micron resolution (~40 nm) (Sakellari et al., 2012)(Li et al., 2009; Kawata et al., 2001; Spangenberg et al., 2013). TPP lithography is hence found to be a cost-effective and straightforward technique since it is based on one-step and mask-less DLW (Sakellari et al., 2012; Li et al., 2009; Kawata et al., 2001; Niesler & Hermatschweiler, 2015). 3D micro/nano structures fabricated by TPP technique can be hugely employed in numerous applications such as microfluidics, bioelectronics, and energy storage devices as the photo-curable inks can be tuned in terms of mechanical, thermal, optical, electrical and biological properties through being doped with a variety of functional agents such as conductive particles (Masui et al., 2011), semiconductive nanoparticles (Sun et al., 2008), magnetic materials (Xia et al., 2010), biomolecules and proteins (Carlotti & Mattoli, 2019).

Significant efforts have been devoted towards electrical functionalization of TPP-compatible resins to construct conductive microdevices. Both inorganic, i.e., Au (Terzaki et al., 2011; Nakamura et al., 2019; Shukla et al., 2011) and Ag (Liu et al., 2019) nanoparticles, and organic fillers such as graphene (Oubaha et al., 2012), carbon nanotubes (CNTs) (Staudinger et al., 2017; Xiong et al., 2016; Guo et al., 2012), and organic semiconductors (conducting polymers (CPs)) (Kurselis et al., 2013) have been utilized to confer electrical properties to otherwise insulating photoresists and resultant TPP-fabricated structures (Carlotti & Mattoli, 2019). Although metallic fillers improve the electrical conductivity, refraction index of metals can interfere with the laser by creating local heat in the resin (Carlotti & Mattoli, 2019), which leads to structural deformation and reduces the quality of fabricated microstructures. Alternatively, assembly of organic fillers in TPP-compatible resins and/or TPP-fabricated structures has been a popular choice for development of next-generation microelectronic devices such as actuators, sensors, and neural microelectrodes (Xiong et al., 2016; Tao et al., 2019a), mainly due to their ease of fabrication, desirable mechanical properties, and biocompatibility. However, the range of electrical conductivity reported through incorporation of carbon-based fillers in TPP-compatible resins has remained significantly low. For example, Xiong et. al. have reported that conductivity of microstructures reached 46.8 S m$^{-1}$ by incorporation of 0.2 wt % CNTs in an acrylate monomer resin (Xiong et al., 2016), indicating that achieving higher levels of conductivity is critically challenging.

Organic semiconductors such as poly(3,4-ethylenedioxythiophene) (PEDOT) have attracted considerable attention due to their soft mechanical properties, mixed ionic/electronic conduction, outstanding chemical stability, biocompatibility, and ease of synthesis (Guimard et al., 2007; Long et al., 2011; Malliaras & Abidian, 2015; Antensteiner et al., 2017; Qu et al., 2016). Adjusting the doping level during fabrication allows CPs to exhibit a broad spectrum of electrical conductivity from semiconductors to metals (Green & Abidian, 2015). CPs have therefore been employed in a variety of applications including transistors and energy storage, photovoltaic cells, chemical and biological sensors (Jang, 2006), and biomedical engineering, particularly in neural prosthetics and interfaces (Ludwig et al., 2006; Abidian & Martin, 2009; Abidian et al., 2009) (Abidian et al., 2010; Abidian et al., 2006; Abidian & Martin, 2008). A number of efforts have been explored to functionalize TPP-fabricated microstructures with CPs, including oxidative polymerization of 3,4-ethylenedioxythiophene (EDOT) monomer (Kurselis et al., 2013) and in-situ self-assembly of poly(3,4-ethylenedioxythiophene): poly(styrenesulfonate) (PEDOT:PSS) in microscopic level following (Tao et al., 2019b). In both cases, however, there was no control on incorporation level of CP into the structure, which did not result in significant conductivity improvement. Thus, there clearly is a need for further research in order to bring these efforts to fruition.

SUMMARY

Thus, in accordance with the present disclosure, there is provided a two-photon polymerization (TPP) compatible photosensitive ink or resin, wherein said ink or resin comprises at least one organic semiconductor, crosslinker, photoinitiator, and solvent. In some aspects, the ink or resin comprises an organic semiconductors, a crosslinker, a photoinitiator, and a solvent. In certain aspects, the ink or resin comprises two organic semiconductors, a crosslinker, a photoinitiator, and two solvents. The crosslinker may be polyethylene glycol diacrylate (PEGDA), the organic semiconductor may be poly (3,4-ethylenedioxythiophene)-poly (styrenesulfonate) (PEDOT:PSS), the photoinitiator may be ethyl (2,4,6-trimethylbenzoyl) phenylphosphinate (T-POL), and/or the solvent may be dimethyl sulfoxide (DMSO). The crosslinker may be PEGDA, the organic semiconductors may be poly (3,4-ethylenedioxythiophene)-poly(styrene-sulfonate) (PEDOT:PSS) and multi-walled carbon nanotubes (MWCNTs), the photoinitiator may be T-POL, and/or the solvents may be DMSO (e.g., for the PEDOT:PSS) and pentaerythritol tetrakis(3-mercaptopropionate) (PETMP) (e.g., for the MWCNTs). The solvent may be present at 25-45 wt %, the PEPDOT:PSS is present at 0.1-0.5 wt %, the crosslinker is present at 72.5-72.9 wt %, and/or the photoinitiator is present at 2 wt %. The PETMP may be present at 18.75 wt %, DMSO may be present at 24.7-24.9 wt %, the PEPDOT:PSS may be present at 0.1-0.4 wt %, MWCNT may be present at 0.05-0.15 wt %, the crosslinker may be present at 54 wt %, and/or the photoinitiator may be present at 1.95 wt %. The ink or resin may be in the form of a homogenous liquid or a solid.

The ink or resin may further comprise a biologically active agent and/or a chemical species, such as where the biologically active agent a protein, a nucleic acid, a carbohydrate or a lipid, more particularly an extracellular protein (laminin, collagen, fibronectin, elastin, proteoglycan, etc.), a growth factor (ephrin, fibroblast growth factor, glial cell derived neurotrophic factor, human growth hormone, neurotrophins, etc.), an enzyme (urease, urate oxidase, glucose oxidase, lactose oxidase), a neurotransmitter (dopamine, aspartate, glutamate, serotonin, etc.), a cell adhesive protein or peptide, or a glycosaminoglycan. The biologically active molecules may be present at 1-300 µg ml$^{-1}$ (e.g., laminin) and/or 100-4000 KU ml$^{-1}$ (e.g., GOx) in the ink. The chemical species may be an ion (Na+, Cl−, K+, etc.).

Also provided is a fabricated device composed of the ink or resin as described herein. The device may comprise a three-dimensional structure such as conductive filler (carbon nanotubes, graphene, nanoparticles, etc.), a semiconductive nanoparticle, or a magnetic particle, and may be a TPP-fabricated microdevice. Incorporation of 0.1-0.5 wt % PEDOT:PSS may provide an electrical conductivity of 10 orders of magnitude from insulating up to 27000 S m$^{-1}$. Incorporation of 0.1-0.4 wt % PEDOT:PSS and 0.05-0.15 wt % MWCNTs may provide an electrical conductivity of 10 orders of magnitude from insulating up to 140000 S m$^{-1}$. The device may be a micro/nanoelectronic, a battery, an optic element, a flexible electronic device, a printed circuit board, a chip-scale electronic, a chemical/biological sensor, a micro/nano electromechanical system, an organic bioelectronic, a neural interface, a neural recording and/or stimulation device, a wearable biosensor, a bioactuator, a soft robotic, a tissue engineering scaffold, or a bioprinted organ. The device may be a next-generation electroactive microdevices which can be employed as chip-scale circuitry, actuators, biosensors, or neural interfaces.

In another embodiment, there is provided a method of preparing an ink or resin of the present embodiments and aspects thereof comprising adding in the following order:
(i) the PEDOT:PSS,
(ii) the solvent;
(iii) the crosslinker; and
(iv) the photoinitiator; or
(i) the MWCNTs,
(ii) the solvent for MWCNTs;
(iii) the PEDOT:PSS,
(iv) the solvent for PEDOT:PSS;
(v) the crosslinker; and
(vi) the photoinitiator.

The method may further comprising adding, after the photoinitiator, a biologically active substance, a chemically active substance or a three-dimensional structure. The method may further comprise coating a surface with said ink or resin and activating said photoinitiator.

In still another embodiment, there is provided a method of detecting an analyte in sample or subject comprising contacting said sample or subject with a device coated with a two-photon polymerization (TPP) compatible photosensitive ink or resin, wherein said ink or resin comprises at least one organic semiconductor, crosslinker, photoinitiator, and solvent and a biological molecule that binds and/or reacts with said analyte to produce a detectable event. The ink or resin may comprise two organic semiconductors, a crosslinker, a photoinitiator, and two solvents. The ink or resin may comprise an organic semiconductor, a crosslinker, a photoinitiator, and a solvent. The analyte may be glucose and said biological molecule is glucose oxidase.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

It is contemplated that any method or composition described herein can be implemented with respect to any other method or composition described herein. Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings form part of the present specification and are included to further demonstrate certain aspects of the present disclosure. The disclosure may be better understood by reference to one or more of these drawings in combination with the detailed description of specific embodiments presented herein.

(FIG. 1A) Components of the OS composite resin: photopolymer poly(ethylene glycol) diacrylate (PEGA), organic semiconductor (OS) poly(3,4-ethylenedioxythiophene):poly(styrenesulfonate) (PEDOT:PSS), photoinitiator 3-(trimethoxysilyl)propyl methacrylate (T-POL), miscible agent dimethyl sulfoxide (DMSO) and proteins such as laminin and glucose oxidase. (FIG. 1B) Experimental setup for the MPL process, including resin, glass/PDMS substrates, 3D piezostage, controller, femtosecond (fs) laser, and the objective lens. (FIG. 1C) The OS composite resin (yellow color) is crosslinked by a focused fs laser to create 3D OSCMs (green color). (FIG. 1D) The sample is then rinsed in ethanol to remove any unsolidified resin, leaving the 3D OSCMs on the substrate.

(FIG. 2A) Thin and flexible PDMS substrate used for MPL fabrication. (FIG. 2B) Optical microscopy micrograph of a micro-grid fabricated on PDMS film shown in (A). (FIGS. 2C-F) Scanning electron microscopy (SEM) micrographs of various microstructures, including a micro-snowflake (FIG. 2C), micro-spring (FIG. 2D), micro-honeycomb (FIG. 2E), and vertical micro-tubes (FIG. 2F). (FIG. 2G) Optical transparency of the resin with various OS concentrations in the 350-750 nm wavelength spectrum. Black squares, red circles, blue up-sided triangles, magenta down-sided triangles, green diamonds, dark blue left-sided triangles, and royal right-sided triangles represent polymer (resin without DMSO), 0 wt % OS, 0.1 wt % OS, 0.2 wt % OS, 0.3 wt % OS, 0.4 wt % OS, and 0.5 wt % OS, respectively. (FIG. 2H) Transmittance of resins at 550 nm with respect to various OS concentrations. Data shown as mean±SEM, n=3.

(FIG. 3A) FTIR spectra of pure OS (blue curve), OS composite polymer (red curve) and polymer (black curve) microstructures. (FIG. 3B) Electrical conductivity of OSCMs with respect to OS concentration in the resin. Data shown as mean±SEM, n=9, * p<0.001. (FIGS. 3C and D) OS composite polymer structures (FIG. 3C) and polymer structures (FIG. 3D) acting as interconnects to drive a LED, respectively (scale bars: 5 mm). (FIG. 3E) Schematic of proposed conductivity of MPL-fabricated OS composite polymers. (FIG. 3F) 3D view of color-coded height maps of cubic microstructures fabricated using OS composite resin (0.5 wt % OS), showing surface texture of MPL-fabricated microcubes. (FIG. 3G) Surface roughness (Rrms) with respect to OS concentration. Data shown as mean±SEM, n=4,  p<0.05, *** p<0.001. (FIG. 3H) Comparison between specific conductivity of MPL-fabricated conductive microstructures in this study using OS composite resin and prior works using other conductive nanomaterials and post processing methods (Au NP: gold nanoparticles, Ag NP: silver nanoparticles, CP P.P.: conducting polymer (CP) post-polymerization (P. P.) after MPL fabrication, GP: Graphene, CNT: carbon nanotubes, CNT+CP P.S.: Doping CNT in resin, followed by post soaking of MPL-fabricated structures in CP solution, OS: organic semiconductor). Black squares represent planar structures, black triangles represent 3D microstructures. (FIG. 3I) Optical microscopy micrograph of a pPCB comprised of various electrical elements. (FIG. 3J) I-V graph of elements in pPCB: a1 (black squares), a2 (red circles), a3 (blue up-sided triangles), and a4 (magenta down-sided triangles); the straight lines indicate the resistor behavior of the elements. (FIG. 3K) SEM micrograph of a microcapacitor array. (FIG. 3L) Hysteresis loop of three microcapacitors in parallel. The rectangular-shaped I-V indicates capacitor behavior.

(FIGS. 4A and B) Fluorescent microscopy micrographs of LM-OSCMs showing the incorporation and distribution of LM. (FIGS. 4C and D) Representative epifluorescence micrographs of endothelial cells fixed and stained with Oregon Green 488 phalloidin (green) and DAPI (red) to visualize F-actin and cell nuclei, respectively after 48 hr cultured on LM-OS microstructures (FIG. 4C) and OS microstructures (without LM) (FIG. 4D) (scale bars: 100 μm). (FIG. 4E) Quantification of (FIG. 4C) and (FIG. 4D) showing the cell density, data shown as mean±SEM, n=3, *** p<0.001.

(FIGS. 5A-C) Schematic illustrations for fabrication of bioelectronics: (FIG. 5A) Construction of insulating electrode shank and base (height: 2 μm) using the polymer resin (without added OS). (FIG. 5B) OSCMs including electrode sites (height: 7 μm, diameters: 1, 5, 10, 20, 40, and 80 μm), interconnect cables (width: 1 μm, height: 2 μm), and contact pads (length: 20 μm, width: 20 μm, height: 7 μm) were fabricated using the OS composite resin (OS concentration: 0.5 wt %). (FIG. 5C) The insulating layer is fabricated using the polymer resin (without added OS) to encapsulate the interconnect cables (height: 3 μm). (FIGS. 5D-F) Schematic illustrations for fabrication of biosensors: following construction of insulating electrode shank and base (height: 2 μm) from the polymer resin without added OS (A), (FIG. 5D) enzyme-loaded sites are fabricated from OS composite resin containing glucose oxidase (GOx), (FIG. 5E) construction of interconnect cables and contact pads using OS composite resin (without enzyme), (FIG. 5F) fabrication of insulating layer. (FIGS. 5G-J) Optical micrograph representations of MPL-fabricated microstructures (scale bars: 50 μm). (FIG. 5G) Representation of schematic FIG. 5A, (FIG. 5H) representation of schematic FIG. 5D, (FIG. 5I) representation of schematic FIGS. 5B and 5E, (FIG. 5J) representation of schematic illustration FIGS. 5C and 5F. (FIGS. 5K-L) Pseudo-colored SEM micrographs of MPL-fabricated microelectrode at low and high magnifications, respectively (green represents polymer and red represents OS composite polymer). Scale bars in K and L are 100 μm and 50 μm, respectively.

(FIG. 6A) Impedance magnitude over a frequency range of $1$-$10^5$ Hz for electrode sites with diameters of: 1 μm (S1, black squares), 5 μm (S2, red circles), 10 μm (S3, blue up-sided triangles), 20 μm (S4, magenta down-sided triangles), 40 μm (S5, green diamond), and 80 μm (S6, dark blue hexagon). (FIG. 6B) Impedance of microelectrode sites at 1 kHz. Data shown as mean±SD, n=3, * p<0.001. (FIG. 6C) Phase angle of the impedance spectrum over the frequency range of $1$-$10^5$ Hz. (FIG. 6D) Cyclic voltammetry of microelectrode sites, with potential swept from −0.8 to 0.4 V and a scan rate of $0.1$ V $s^{-1}$. (FIG. 6E) Charge storage capacity of the microelectrode sites. Data shown as mean±SD, n=3, * p<0.001. (FIG. 6F) Cyclic voltammetry of a microelectrode site in various glucose concentrations: 0.1 mM (black), 0.2 mM (red), 0.5 mM (grey), 1 mM (blue), 2 mM (magenta), and 3 mM (light green). (FIG. 6G) Amperometric current response of OS (blue) and GOx-OS (red) composite microelectrodes to successive glucose addition at polarization potential of +0.3 V vs. Ag/AgCl. (FIG. 6H) Proposed detection mechanism of glucose using MPL fabricated GOx-OSCMs: electrons are transferred from glucose to the OS microelectrodes at +0.3 V vs. Ag/AgCl. (FIG. 6I) Amperometric current response of a GOx-OS composite microelectrode to addition of (1) glucose (0.2 mM), (2) acetaminophen (0.1 mM), (3) ibuprofen (0.1 mM), (4) ascorbic acid (0.1 mM), and (5) urea (0.1 mM), sequentially. (FIG. 6J) The response curve (calibration curve) of the biosensor showed an operating range within 0.1-3 mM glucose concentration (dynamic range of current response 0-2 μA), with a sensitivity of $232.9\pm22.5$ μA $mM^{-1}$ $cm^{-2}$ between 0.1 and 1 mM as shown in FIG. inset. Data shown as mean±SEM, n=4. (FIG. 6K) Sensitivity of glucose biosensors (based on literature search) for different electroactive materials based on amperometric detection of glucose (CP: conducting polymers, CNT: carbon nanotubes, Au: gold, and OS: organic semiconductor). Black squares and black triangles demonstrate physical entrapment and covalent attachment, respectively. Star with red circle background represents the sensitivity of the sensor based on physical encapsulation of GOx in OS composite polymer).

(FIG. 7A) Aggregation of OS in resin without DMSO, and upright micrograph of MPL-fabricated structures using resins with (FIG. 7B) 45 wt % DMSO, (FIG. 7C) 40 wt % DMSO, (FIG. 7D) 37.5 wt % DMSO, and (FIG. 7E) 35 wt % DMSO.

(FIGS. 8A-E) optical micrographs of resin stability over time at 1 h, 10 h, 20 h, 30 h, and 36 h after preparation scale bars: 1 cm). (FIGS. 8F-J) higher magnification optical micrographs of A-E, (scale bar: 1 mm).

(FIG. 10A and FIG. 10B) SEM of MPL-fabricated lines using an oil immersion objective lens 63× (NA 1.4), with laser power of 28 mW and focused scan speed of 100 $\mu$m s$^{-1}$.

(FIG. 11A) MPL-fabricated line on a partially gold-coated coverslip (scale bar: 50 $\mu$m). (FIG. 11B) I-V curves of lines fabricated with resins with various OS concentrations 0 wt % (C0, black), 0.1 wt % (C1, red), 0.2 wt % (C2, blue), 0.3 wt % (C3, magenta), 0.4 wt % (C4, green), and 0.5 wt % (C5, dark blue). Voltage ranged between -3 V and 3 V, while current was automatically recorded.

(FIG. 13A) 3D view of color-coded height map. (FIG. 13B) Color coded surface topography of the cube (area of 50 $\mu$m×50 $\mu$m was extracted for roughness measurements), and (FIG. 13C) Surface roughness profile.

(FIG. 14A) Fluorescent micrograph of LM-OSCMs after immunohistochemistry (IHC). (FIG. 14B) Line intensity scans across (red lines) as indicated in IHC image.

(FIG. 15A) Swelling ratio (%) with respect to time for polymer and OS-polymer composite structures. Data shown as mean±SD, n=5. (FIG. 15B) Impedance of the MPL-fabricated microelectrode site (diameter: 80 $\mu$m) over 3 days (day 1, 2, and 3 are shown by black square, red circle, and blue triangle, respectively. (FIG. 15C) Mass loss (%) of OS composite structures over 10 days. Data shown as mean±SD, n=5, ns represents no significance.

(FIG. 17A) Addition of GOx to the OS resin. (FIG. 17B) Impedance spectrum of OS microelectrode cites (black circles) and GOx-OS microelectrode cites (red square). (FIG. 17C) CV curves of OS microelectrode cites (black curve) and GOx-OS microelectrode cites (red curve).

(FIG. 18A) Viability (normalized with respect to control) comparison between OS composite structures and control on day 0 and day 7. (FIG. 18B). The percentage of activated splenic T cells (assessed using CD69) and B cells (assessed using CD86) after 7 days of culture on OSCM or control structures, as assessed using flow cytometry. OS composite structure and control (without structure) are shown in black and grey bars, respectively. Data shown as mean±SD, n=3, ns represents no significance. The initial cell count was 5000000 cell/ml for all samples, therefore there are no error bars for A at day 0.

(FIG. 20A) Optical micrograph of micro-bridges. (FIG. 20B) Logarithmic conductivity with 10 respect to PEDOT:PSS concentration in the ink (n=9). (FIGS. 20C-D) Application of conductive and non-conductive gel for driving an LED circuit, respectively. Voltage is set at 40 V (scale bars: 5 mm). (FIG. 20E) Illustration of the LED circuit (FIG. 20F) Schematic of conductivity hypothesis. (FIG. 20G) Conductivity of TPP-fabricated microstrucutres with respect to Young modulus of the conductive filler.

(FIG. 21A) Optical micrograph of a PCB. (FIG. 21B) I-V sweep of 4 selected conductive sites in PCB (Site 1, 2, 3, and 4 are represented by black square, red circle, blue up-sided triangle, and magenta down-sided triangle, respectively). (FIG. 21C) SEM of a zig-zag array. (FIG. 21D) Impedance spectrum of a zig-zag line in frequency range of 1-10$^5$ Hz. (FIG. 21E) SEM of a micro-capacitor array. (FIG. 21F) Cyclic voltammetry of a micro-capacitor. In FIG. 21D and FIG. 21F, red circle and black square represent 0.5 wt % PEDOT:PSS-incorporated ink and non-conductive ink, respectively.

(FIGS. 22A-C) Upright micrographs of TPP-fabricated biosensors (scale bars: 50 $\mu$m). (FIG. 22D) Amperometric current response for control cube (green line), cubic biosensor (blue line), grid biosensor with line spacing of 5 $\mu$m (magneta line), and grid biosensor with line spacing of 10 $\mu$m (red line). (FIGS. 22E-F) Zoomed-in upright micrographs of grids with line spacings of 5 $\mu$m and 10 $\mu$m, respectively (scale bars: 20 $\mu$m). (FIGS. 22G-H) Calibration curve and linear range for biosensors, respectively (blue square and line: cube, magneta circle and line: grid with line spacing of 5 $\mu$m, and red triangle and line: grid with line spacing of 10 $\mu$m).

(FIG. 23A) Schematic of two-step fabrication procedure, starting by construction of electrode shank (shown in red) with conductive ink, followed by synthesis of isolation coverage (shown in green) via non-conductive ink. (FIGS. 23B-C) Upright micrographs of the microelectrode after the first and second step of fabrication, respectively. (FIG. 23D) SEM micrograph of hybrid microelectrode. (FIGS. 23E-G) High magnification SEM images of the microelectrode including a cubic pad (FIG. 23E), cylindrical recording site 5 (FIG. 23F), and tip of the electrode (FIG. 23G).

(FIG. 24A) Two steps for preparation of the conductive resin, and (FIG. 24B) Control resin (left) and conductive resin (right). Inclusion of both MWCNT and PEDOT:PSS has given a black color to the resin.

(FIG. 25A) TPP fabrication setup, including stages, sample holder and laser objective, (FIG. 25B) Irradiation of focused fs laser beams crosslinked the resin at the focal point, (FIG. 25C) and (FIG. 25D) Upright micrographs of UH logo and cougar symbol, respectively, (FIG. 25E), (FIG. 25F), and (FIG. 25G) Upright micrographs of micro resistor array, common capacitors, and micro integrated capacitors, respectively.

(FIG. 26A) TPP-fabricated microbars on partially gold-coated coverslips for IV measurements, (FIG. 26B) Electrical conductivity for 4 different ink compositions, (FIG. 26C) Electrical conductivity for various contents of MWCNTs and PEDOT:PSS in the ink (0.05 wt % CNT, 0.1 wt % CNT, and 0.15 wt % CNT are shown in black, blue, and red, respectively), (FIG. 26C) Formation of conductive complexes in microstructures based on PEDOT:PSS/MWCNT-doped resin, and (FIG. 26D) Comparison between obtained electrical conductivities in relevant works.

(FIG. 27A) Impedance spectroscopy over frequency range of $1\text{-}10^5$ Hz, (FIG. 27B) Phase angle of the impedance spectrum, (FIG. 27C) Cyclic voltammetry graph in potential range of $-0.4\text{-}0.8$ V with scanning rate of $0.1$ V $s^{-1}$ (control, 0.15 wt % CNT, 0.4 wt % PP, and 0.4 wt % PP+0.15 wt % CNT compositions are represented in black square, red circle, blue up-sided triangle, and magenta down-sided triangle, respectively), and (FIG. 27D) Box graph of charge storage capacity (black squares, red lines and red whiskers show average, median, and standard deviation, respectively.

DESCRIPTION OF ILLUSTRATIVE EMBODIMENTS

Figures 1A, 1B, 1C, 1D:
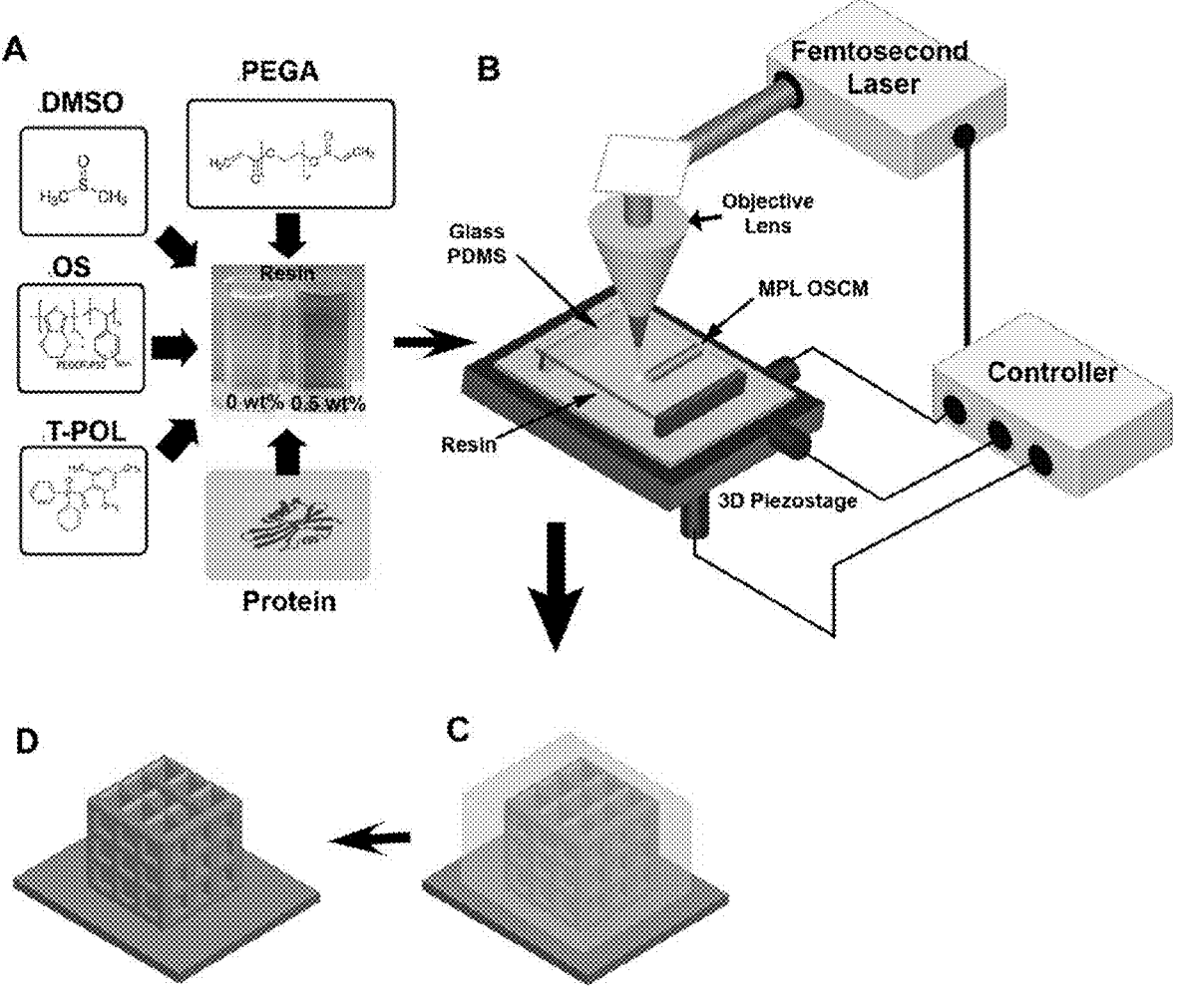
FIGS. 1A-1D: Resin components and MPL fabrication process.

As discussed above, there have been efforts to functionalize TPP-fabricated microstructures with organic semiconductors, including oxidative polymerization of 3,4-ethylenedioxythiophene (EDOT) monomer and in-situ self-assembly of poly(3,4-ethylenedioxythiophene): poly(styrenesulfonate) (PEDOT:PSS) in microscopic level following. In both cases, however, there was no control on incorporation level of conducting polymers into the structure, which did not result in significant conductivity improvement.

To address this challenge, here the inventors introduce a novel ink which can be fabricated into highly conductive and bioactive 3D microstructures via TPP. For the first time, the inventors report that direct incorporation of PEDOT:PSS in a polyethylene glycol diacrylate (PEGDA)-based ink remarkably improves the conductivity of TTP-fabricated structures over 10 orders of magnitude, and almost doubles the Young Modulus. In vitro studies demonstrate that presence of laminin, a well-known cell adhesive protein, in the ink encourages cellular attachment to TPP-fabricated constructs. Furthermore, the inventors have established a novel and straightforward methodology for fabrication of hybrid (combination of conductive/nonconductive material) microelectronic devices such as neural microelectrode arrays on flexible substrates. Conductive and bioactive microstructures based on the PEDOT:PSS/laminin-doped ink are promising for a variety of applications, ranging from chip-scale electronics and flexible circuit boards to wearable biosensors and neural interfaces.

The resulting resin is inherently conductive, owing to the presence of PEDOT:PSS, and can be directly fabricated into conductive microstructures. The obtained conductivity is >104 S/m, which is almost 4 orders of magnitude higher than related materials. Furthermore, direct incorporation of enzymes (e.g., glucose oxidase) leads to development of high-performance biosensors (e.g., for glucose). Also, high resolution (down to 1 μm in X, Y and Z axes) can be achieved.

Further, the inventors have also developed and characterized a photosensitive resin based on composite organic fillers, i.e. PEDOT:PSS and MWCNT. For the first time, it is demonstrated that direct incorporation of 0.4 wt % PEDOT:PSS and 0.15 wt % MWCNTs in a polyethylene PEGDA-based resin remarkably enhances the conductivity of TPP-fabricated microstructures over 10 orders of magnitude. The obtained electrical conductivity of the composite microstructures was increased over other formulations. Electrochemical analysis revealed that PEDOT:PSS/MWCNT-incorporated microstructures exhibit low impedance and high charge storage capacity.

These and other aspects of the disclosure are described in detail below.

I. TWO-PHOTON POLYMERIZATION

Two-photon polymerization is a non-linear optical process based on the simultaneous absorption of two photons in a photosensitive material (photoresist). This process changes the photosensitive material, i.e. it leads to a polymerization by activating so-called photo-initiators in the resist. These turn into radicals that polymerize the resist locally. In a subsequent step, the non-polymerized photoresist is washed out to uncover the structure. The material of the structures is not restricted to just polymers but can be converted for example into silicon via a secondary chemical process.

Two-photon polymerization as a direct laser writing technique allows for creating complex three-dimensional structures down to feature sizes on the order of 100 nm. Key elements of two-photon polymerization are lasers providing femtosecond pulses, suitable photosensitive materials (photoresists), a precise positioning stage and a computer to control the procedure.

Two-photon absorption requires high intensities that are provided by a tightly focused femtosecond laser beam. As two-photon absorption is proportional to the square of the intensity, it only takes place in the focus providing high spatial resolution. Accordingly, the resist polymerizes only in the ellipsoidal focus, termed "voxel" (abbr. for volume pixel). Scanning the laser through the resist in all three dimensions "writes" the desired structure voxel by voxel. During two-photon polymerization the surrounding oxygen quenches the radicals to a certain extent. This results in feature sizes down to ~100 nm. Another advantage of 2-photon polymerization is that many polymers have "next to none" linear absorption in the near-infrared, allowing the laser to penetrate deeply into the material. These two aspects allow creating nanostructures that are otherwise not possible to produce.

Computer-aided exposure of a multitude of photoresists as well as established 3D casting techniques make direct laser writing an indispensable tool for a large variety of applications in life sciences such as extracellular matrices, lab-on-a-chip applications (opto-)electronics or photonics such as photonic crystals.

II. INK/RESIN

In an embodiment, the conductive inks/resins of the disclosure contain DMSO (25 wt %), PEDOT:PSS (0.1-0.5 wt %), and PEGDA (72.5 wt %). Non-conductive resins included neither PEDOT:PSS nor DMSO. In embodiments, liquid resins composed of a constant amount of T-POL (2 wt %). The components may be added in the order of: 1) PEDOT:PSS, 2) DMSO) 3) PEGDA, 4) T-POL, and 5) Laminin/GOx. The mixture may be magnetically stirred for about 2 hours, followed by about 1 hour of degassing, such as by using a desiccator. Since the inks are photosensitive, containers should be covered with aluminum foil and kept away from ambient light. Functionalized inks can also be prepared, in certain embodiments, by adding Laminin (100 $\mu$g ml$^{-1}$) or GOx (3.5 KU ml$^{-1}$) to the conductive ink (containing 0.5 wt % PEDOT:PSS) using a vortex mixer for 30 s.

In another embodiment, the composite ink may comprise PEDOT:PSS and MWCNT. The initial resin may comprise MWCNTs, PETMP, TPO-L, and PEGDA. After 10-12 h of magnetic stirring, the mixture may be centrifuged for 30 min at 4700 rpm (Allegra X-30R, BECKMAN COULTER) to remove large CNT aggregates. Lastly, DMSO and PEDOT:PSS may be added to the resin, which may then be stirred for 1 h. Hence, the final resin may comprise PEDOT:PSS (0-0.4 wt %), DMSO (24.6-25 wt %), MWCNTs (0-0.15 wt %), PETMP (18.75 wt %), T-POL (2 wt %), and PEGDA.

III. ADDITIONAL MATERIALS FOR INCLUSION IN INK/RESIN

The disclosure also provides for ink/resins that are doped with various molecules such as extracellular proteins (collagen, fibronectin, elastin, proteoglycans, etc.), growth factors (ephrins, FGF, GDNF, HGF, neurotrophins, etc.) enzymes (urease, urate oxidase, glucose oxidase, lactose oxidase), neurotransmitters (dopamine, aspartate, glutamate, cewrotonin, etc.), cell adhesive proteins and peptides, glycosaminoglycans (GAGs) and ions (Na+, Cl–, K+, etc.) Moreover, other conductive fillers (such as carbon nanotubes, graphene, metallic nanoparticles), semiconductive nanoparticles, and magnetic materials can be incorporated into the ink/resin to tune the desirable properties of the TPP-fabricated microstructures.

IV. DEVICES AND APPLICATIONS

The conductive and bioactive TPP-fabricated microstructures based on PEDOT:PSS and PEDOT:PSS/MWCNTs-doped ink can be utilized in many diverse applications, including micro/nanoelectronics, charge storage and cellular batteries, optics, flexible electronics, printed circuit boards and chip-scale electronics, chemical/biological sensors, micro/nano electromechanical systems, organic bioelectronics, neural interfaces, neural recording and stimulation, wearable biosensors, bioactuators and soft robotics, tissue engineering scaffolds, and organ bioprinting.

V. EXAMPLES

The following examples are included to demonstrate preferred embodiments. It should be appreciated by those of skill in the art that the techniques disclosed in the examples that follow represent techniques discovered by the inventor to function well in the practice of embodiments, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1—Materials and Methods

Materials. Poly(ethylene glycol) diacrylate ($M_n$=700), high conductivity grade of Poly(3,4-ethylenedioxythiophene)-poly(styrenesulfonate) 1.0 wt. % in $H_2O$, 3-(Trimethoxysilyl)propyl methacrylate, laminin from Engelbreth-Holm-Swarm murine sarcoma basement membrane (L2020), anti-laminin antibody produced in rabbit, bovine serum albumin (BSA) lyophilized powder ($\geq$96%, agarose gel electrophoresis), D-(+)-Glucose, and Glucose Oxidaze (type X-S from *Aspergillus niger*) were all purchased from Sigma Aldrich. Dimethyl sulfoxide (molecular biology grade), phosphate-buffered saline (PBS) tablets (100 ml-biotechnology grade), ethanol (200 proof), and SYL-GARD™ 184 Silicone Elastomer (Electron Microscopy Science) were ordered from VWR. Ethyl (2,4,6-trimethylbenzoyl) phenylphosphinate was purchased from Oakwood Chemical. Goat anti-Rabbit IgG (H+L) SUPERCLONAL™ Secondary Antibody (Alexa Fluor 488) was purchased from ThermoFisher Scientific. Acid-functionalized multi walled carbon nanotubes (MWCNTs) (purity<95 wt %, outer diameter<8 nm, length: 10-30 um, COOH content: 3.86 wt %) were provided by Cheap Tubes.

Ink formulation and preparation. Conductive resins contained DMSO (25 wt %), PEDOT:PSS (0.1-0.5 wt %), and PEGDA (72.5-72.9 wt %). Non-conductive resins included neither PEDOT:PSS nor DMSO. In all formulations, liquid resins composed of a constant amount of T-POL (2 wt %). The components were added in the order of 1. PEDOT:PSS, 2. DMSO, 3. PEGDA, 4. T-POL, and 5. Laminin/GOx. The mixture was magnetically stirred for 2 hours, followed by 1 hour of degassing, using a desiccator. Functionalized inks were prepared by addition of laminin (100 $\mu$g ml$^{-1}$) or GOx (2000 U ml$^{-1}$) to the conductive ink (containing 0.5 wt % PEDOT:PSS) using a vortex mixer for 30 s.

In the composite photosensitive ink, comprising both MWCNts and PEDOT:PSS, ink preparation consisted of two main steps. First, a mixture of MWCNTs, pentaerythritol tetrakis(3-mercaptopropionate) (PETMP), T-POL, and PEGDA was magnetically stirred for 12 h. To maximize the incorporation concentration, acid-purified MWCNTs (3.86 wt % content of carboxyl groups) with short length (10-30 $\mu$m) were used. There is a trade-off between MWCNT length and electrical properties in polymeric matrices. PETMP was used to disperse MWCNTs in PEGDA blend. The branched thiol groups in PETMP interacted with functionalized carboxyl groups in MWCNTs, making them miscible in PEGDA matrix. Following 12 h stirring, MWCNT aggregates were removed from the mixture through centrifugation. In the second step, dimethyl sulfoxide (DMSO) and (PEDOT:PSS) were added to the ink, which was then stirred for 2 h. The reason for adding DMSO was to maximize the solubility of PEDOT:PSS in the ink through hydrogen bonding between sulfonic acid groups in PSS and SO groups in DMSO. The final resin was therefore composed of two carbon-based conductive fillers, i.e. MWCNTs and PEDOT:PSS, in a highly homogenized PEGDA-based composite.

MWCNTs needed at least 10 h of stirring to become homogenized in the resin by dissolving in PETMP. In contrast, PEDOT:PSS became miscible in the resin within 2 h through addition of DMSO, and prolonged stirring resulted in formation of aggregated PEDOT:PSS particles. Hence, in the case of adding all elements together, by the time MWCNTs were homogenized, PEDOT:PSS was aggregated and removed from the mixture via centrifugation, thus a two-step strategy was used for ink preparation.

PDMS molding. A blend of 1:10 curing agent: PDMS base elastomer (mass ratio) was prepared and well mixed, followed by degassing for 1 hour. The mixture was then poured in a glass mold, followed by heat treatment in oven at 60° C. for 2 hours. Thin and flexible PDMS film (thickness of 0.2 mm) was then detached from the glass.

Fabrication of gold-coated substrates. First, glass coverslips were partially masked by temperature-resistant tape, followed by electron beam evaporative deposition (Thermionics eBeam Evaporator, Thermionics) of a thin layer of chromium (10 nm) and gold (100 nm), respectively. Chrome acted as an intermediate layer to improve attachment of gold to glass.

Surface treatment. In order to facilitate the adhesion of 3D microstructures to PDMS film/glass coverslip, surface plasma oxidation and salinization treatment were performed prior to TPP fabrication. The substrate was first exposed to plasma (115 V, 50/60 Hz, 0.35 Å) for 1 min, using a Handheld Corona Surface Treater (BD-20, ELECTRO-TECHNIC PRODUCTS, INC.). Salinization solution was prepared by adding 100 μL of 3-(Trimethoxysilyl)propyl methacrylate to 2 mL ethanol, and 6 ml diluted acetic acid (1:10 glacial acetic acid:water). 200 μL of solution was added to the surface of substrates. After 5 minutes, the excess solution was poured off, followed by a gentle rinse in ethanol to remove the residual reagent from the surface.

Two-photon polymerization. A droplet of the ink (~5 μl) was loaded between a glass slide and salinized PDMS film/coverslip which were attached to one another by double-sided tape supports. The specimen was positioned on the sample holder located on top of a piezo stage (VP-5ZA, Newport), which was connected to XY-stages (XMS 160, Newport). Two-photon polymerization laser (MAI TAI™ DeepSee, Spectra Physics), operating via MAI TAI™ software 20 (version 2.0), was focused at the interface of PDMS film/coverslip through a 63× oil-immersion objective (Plan N, OLYMPUS). Resin was crosslinked by irradiation of 130 femtosecond laser beams (wavelength: 800 nm, power:1.7 mW) through Ti-sapphire oscillator operating at 80 MHz repetition rate, and simultaneous 3D movement of XYZ-stages resulted in layer by layer construction of the 3D microstructure upside down on PDMS film/coverslip. XYZ-stages were connected to a motion controller/driver (XPS, Newport) and their movement was adjusted by nFab software (version 5.0.14, Newport). Structures were designed by AUTODESK® Fusion 360™ software and the sketches were converted into stereolithography format prior to being imported to nfab. Microstructures were fabricated at scanning rate of 20 μm s⁻¹ and after completion of TPP-fabrication, PDMS film/coverslip was detached from the supports and soaked in ethanol for 1 min to wash off the remaining uncrosslinked resin.

Conductivity/conductance measurement. Semiconductor Device Parameter Analyzer (B1500A, Keysight) was used for electrical measurements. Briefly, probe tips (Signatone, diameter: 1 μm) of two electrodes connected to Source Measurement Unit (SMU-8, Keysight) were placed on two sides of the gold-coated coverslip. Probe movement was thoroughly adjusted using micromanipulators and a Stereo microscope (Discovery. V8, ZEISS Germany) at 8×. I-V sweep was performed by applying a voltage in the range of –3 V to 3 V (increasing step: 50 mV), and current was automatically recorded. EasyEXPERT group+ software (resident GUI-based, Keysight Technologies Inc.) was used to analyze the data. In the case of printed circuit board, probes touched both ends of cube-cylinder sites simultaneously, followed by I-V sweep. Conductance was derived from the slope of the I-V curve, and conductivity was calculated based on the geometry of the structure.

LED circuit setup. Cathode wire of the Micro LED was cut in half and both ends were placed inside a hollow cylindrical PDMS molds with height and diameter of 5 mm. Resin was then poured in the mold and exposed to long wave ultra violet lamp (Black-Ray, model B 100 AP), which crosslinked the resin instantly. The gel was removed from the mold and two ends of the circuit were connected to anode and cathode probes of Semiconductor Device Parameter Analyzer which applied a controlled voltage in the range of 0-40 V.

EIS and CV. Both measurements were conducted by Autolab PGSTAT 302N (USA METROHM Company) and Nova Frequency Response Analyzer software (version 2.1) in potentiostatic mode. A solution of 0.1 M PBS (pH=7.4) was used as the electrolyte media. Three-electrode configuration setup including Ag/AgCl reference electrode, platinum foil counter electrode, and one end of the microstructure (fabricated on the coverslip) were immersed in the PBS solution, while the other end was connected to the working electrode outside of the electrolyte. In EIS, a sinusoidal AC signal with 10 my rms amplitude was imposed to measure the impedance over a frequency range of 1-10⁵ Hz. In CV staircase analysis, the potential of the working electrode was swept in the range of –0.08 V to 0.4 V with respect to the reference electrode at a constant scan rate of 0.1 V S⁻¹. In each experiment, CV was repeated for three times and the third cycle was used to plot CV curve and calculate charge storage capacity since the readings were found to be consistently stable after the second cycle.

Immunohistochemistry (IHC). In order to detect laminin on/within TPP-fabricated microstructures, IHC was performed in the following order: (1) 0.01 M of blocking agent solution (BSA diluted in 1×PBS) was added to the surface of substrate. After 30 minutes of incubation in room temperature, substrate was gently rinsed in deionized water (DIW); (2) Primary anti-body solution (with volume dilution ratio of 1:30 in 1×PBS) was added to the substrate and it was then kept at 4° C. temperature overnight; (3) Substrate was triple washed in DIW (each wash took 20 seconds); (4) Secondary anti-body solution (volume dilution ratio of 1:100 in 1×PBS) was added to the substrate and was incubated for 60 min at room temperature. As of this step, the sample was kept in dark; (5) finally, the substrate was triple washed in DIW and it was ready for fluorescent imaging.

Optical/confocal microscopy. Optical micrographs were captured by upright microscope (Imager Z1, ZEISS Germany) and confocal images were taken by confocal microscope (LSM 800, Observer. Z1, ZEISS Germany). In both cases, ZEN-pro Axiovision digital processing software (ZEIZZ Germany) was used to analyze the images. For fluorescent imaging, fluorescent-tagged laminin was detected using UV light bulb (X-Cite, SERIES 120 Q, LUMEN DYNAMICS) in green fluorescent protein mode and Alexa Fluor 488 detection channel at exposure time of 1000 ms.

Figures 5A, 5B, 5C, 5D, 5E, 5F, 5G, 5H, 5I, 5J, 5K, 5L:
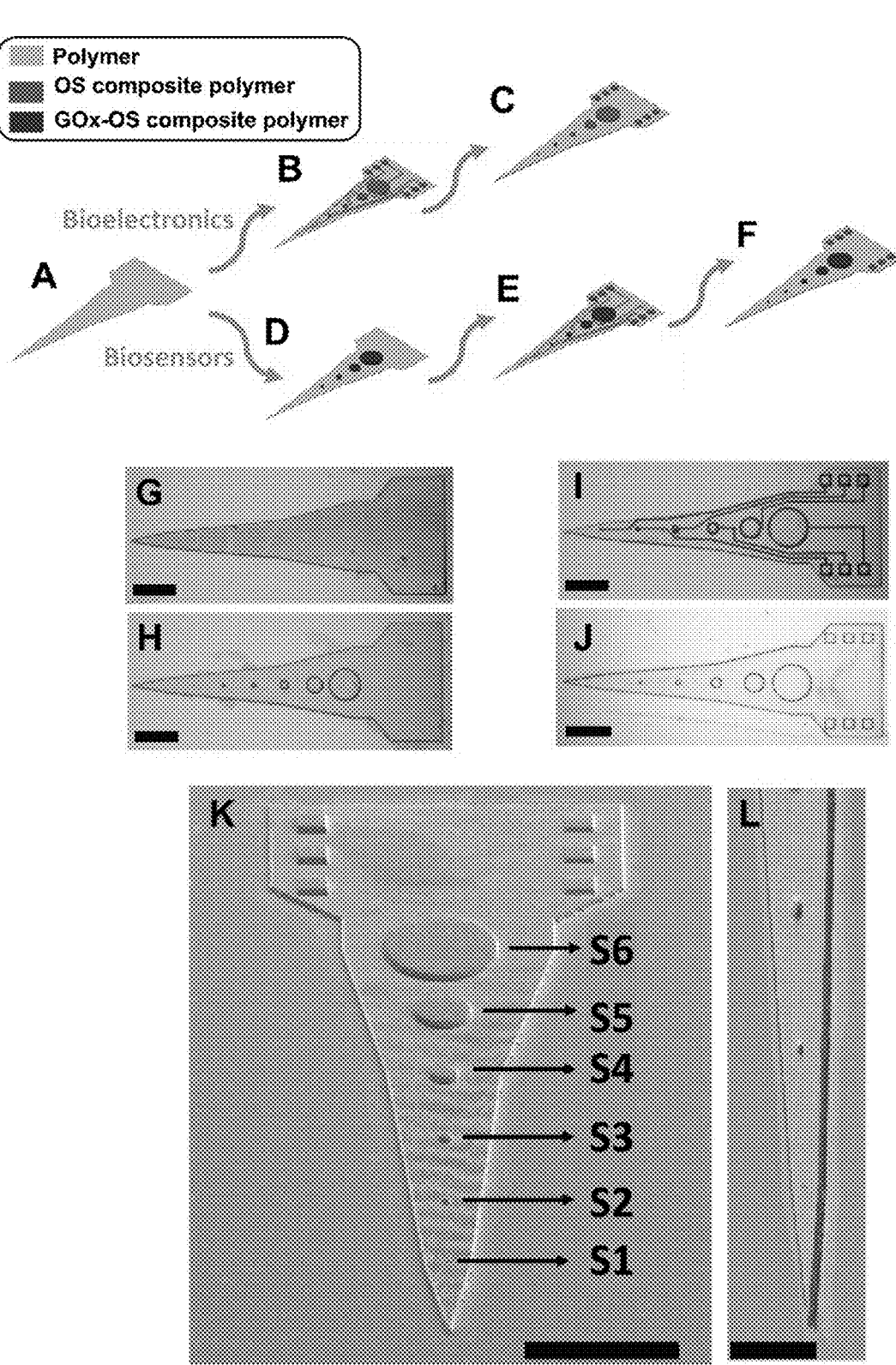
FIGS. 5A-5L: MPL-based Fabrication process of hybrid Michigan-style microelectrode for bioelectronics and biosensors applications.

SEM imaging. Coverslips were mounted on aluminum stubs by double-sided carbon tape and were then sputtered with gold using desktop sputtering system (DESK-II, Denton Vacuum LLC) for 60 s at 40 mA to reduce charging effects. Scanning electron microscope (XL-30S FEG, FEI) was employed to capture images in secondary electron detection mode and operation voltage of 5 kV. Adobe Photoshop software was used to modify brightness/contrast of SEM images, as well as in FIG. 5D. FIG. 5E, FIG. 5F, and FIG. 5G, where segments were artificially colored in red/green for better illustration of conductive/non-conductive material.

AFM. First, a microarray containing 16 cubes with dimensions of 110×10×1 $\mu m^3$ (length×width×height) was fabricated for 2 groups, having either none or 0.5 wt % PEDOT:PSS in the ink.

Cell culture. First, 5 by 5 array of connected cubes with dimensions of 50 $\mu m$×50 $\mu m$×2 $\mu m$ (length×width×height) was 3D printed via TPP, which provided a total area of 500 $\mu m$×500 $\mu m$. The structures were fabricated using conductive inks either with or without laminin incorporation. Following TPP fabrication, samples were soaked in ethanol for 2 hours to make sure DMSO is completely removed from the structure.

Degradation Studies. Arrays of cylindrical OS composite polymers were fabricated and then were soaked in ethanol for 2 h to remove any excess compounds. The initial mass (W0) of the samples was recorded using a Mettler Toledo (XPR504S). The samples were then incubated at 37° C. in 1 mL of PBS (pH=7.4) for different amount of time until swelling ratio and mass loss analysis at the desired time point. At the designated time points, swollen samples (n=5) were removed from the PBS and then rubbed gently with a Kimwipe to remove any excess water. The samples then were weighed to measure the swollen mass (Ww). The samples were then dried in a vacuum oven and were weighed again (Wd). The mass loss and the swelling ratio percentages of the samples were calculated with the following equations.

$$\text{Mass loss } \% = \frac{(W_0 - W_d)}{W_0} \times 100$$

$$\text{Swelling ratio } \% = \frac{(W_w - W_d)}{W_d} \times 100$$

Amperometric response measurements. BioStat™ (ESA Biosciences, Inc.) was used to record the current response at polarization potential of 700 mV vs. Ag/AgCl, which was applied to the biosensor in a stirred solution of PBS (lx, pH=7.4) while successive injections of glucose solution were added (cumulative concentration ranging from 0.1 mM to 20 mM). In the three-cell configuration, counter electrode was Pt wire, and Ag/AgCl reference electrode was used. The resulting current measurements were used to calculate the sensitivity and LOD of the biosensor.

Spleen Cell Culture and Flow Cytometry. Spleen cells were isolated from 3-month-old C57/B6 mice. Briefly, the spleen was dissected and minced through a 70 m sieve and red blood cells were lysed using RBC lysis buffer. After washing and counting cells using Cellometer (Nexcelom Bioscience), spleen cells were cultured in RPMI 1640 media with 10% fetal bovine serum either without (control) or with exposure to OS composite polymer. After 7 days of exposure, the immune cell numbers were counted and analyzed by flow cytometry using the following antibodies, FITC anti-mouse CD3 antibody and PE anti-mouse CD69 antibody, APC Cy7 rat anti-mouse CD45R antibody, and FITC rat anti-mouse CD86 Antibody. All mouse handling and cell isolation procedures were approved by the IACUC at University of Houston.

Figures 7A, 7B, 7C, 7D, 7E, 8A, 8B, 8C, 8D, 8E, 8F, 8G, 8H, 8I, 8J:
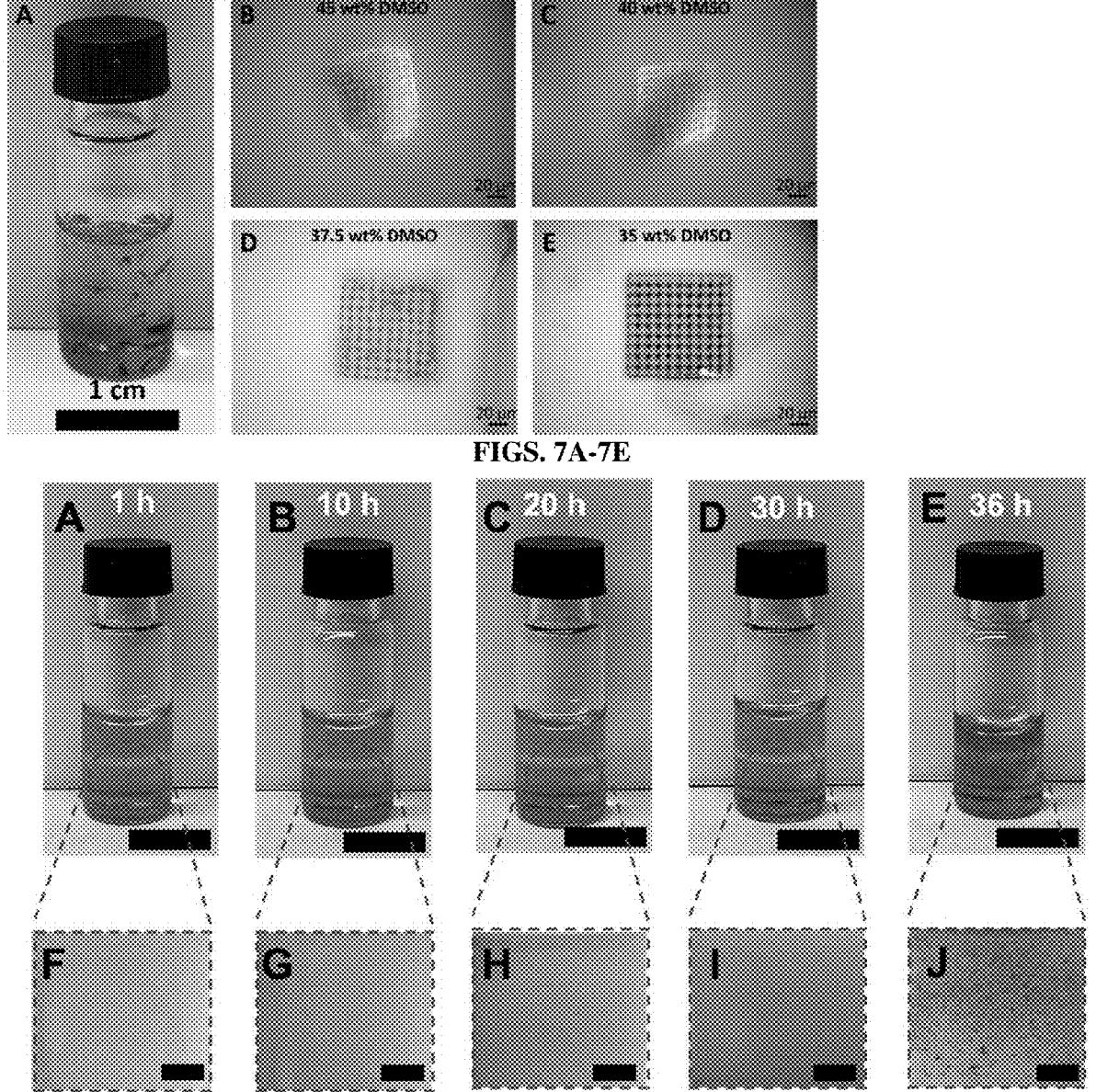
FIGS. 7A-7E: Role of DMSO in the resin formulation.
FIGS. 8A-8J: Resin stability and homogeneity.
Figures 10A, 10B:
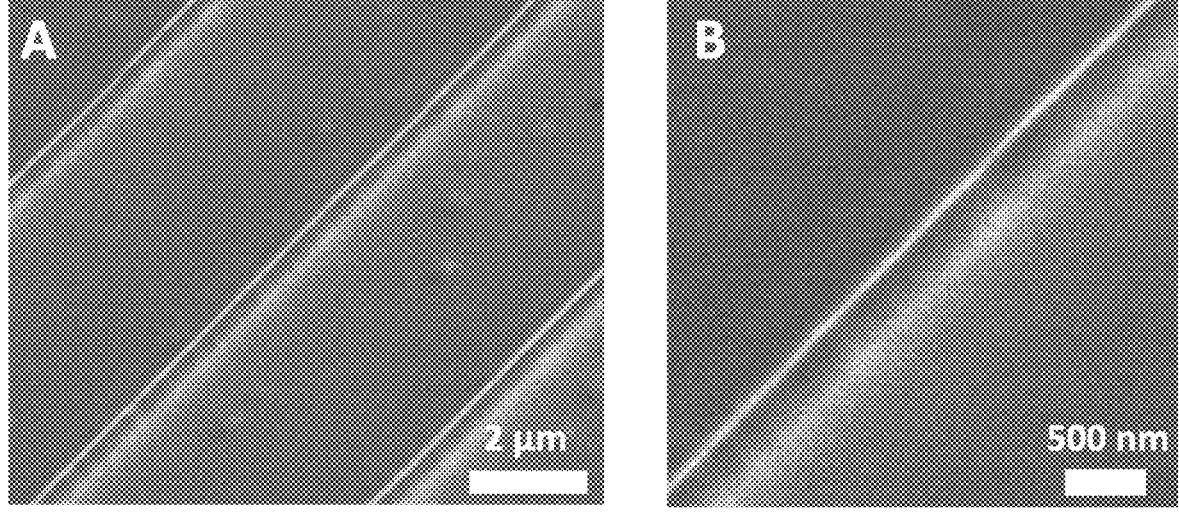
FIGS. 10A-10B.

Statistical analysis. Origin Pro software (2018, Northampton, MA) was used to find significance level between sample groups by one-way ANOVA and Post-Hoc test (Tukey's test), as well as calculation of surface area under the CV curve for capacitance (related to FIG. 3F) and CSC (FIG. 7E). Data are reported in average±standard error of mean in FIG. 2B (n=9, 3 preparations and 3 different samplings), biosensor sensitivity (related to FIG. 5G and FIG. 5H) (n=3), FIG. 7B (n=3), FIG. 7E (n=3), and FIGS. 10B and 10C (n=5). Site conductance (related to FIG. 3B) is reported in average±standard deviation (n=5). LOD of glucose biosensors are calculated based on n=3. Impedance at 910 for zig-zag lines (related to FIG. 3F) and capacitance of micro-capacitors (related to FIG. 3F) are reported in ±standard deviation (n=3). Symbol *** represents significance level of p<0.001.

Example 2—Results

FIGS. 1A-D illustrate the chemical components of the composite resin and the MPL experimental procedure for fabrication of conductive microstructures. The composite resin was prepared by direct addition of a mixture of OS and DMSO to PEGA/T-POL. The reason for choosing DMSO is the miscibility of the OS, PEGA, and T-POL in DMSO in order to prepare a homogeneous and transparent MPL-compatible resin (FIG. 1A). It was observed that in the absence of DMSO, OS would immediately aggregate, revealing the importance of DMSO in complete dispersion of OS (FIG. 7A). The photoinitiator T-POL was used due to its water solubility, biocompatibility, high initiation efficiency, and large absorbance wavelength 600-810 nm (Coleman et al., 1998; Carlsson et al., 1981). To demonstrate its potential application, the OS composite resin was further modified with proteins such as laminin and glucose oxidase (blue box in FIG. 1A). During the MPL process, a femtosecond laser beam (center wavelength of 780 nm, pulse width of 130 nm, repetition rate of 80 MHz, and power of 20 mW) was tightly focused by an objective lens (40×, numerical aperture (NA) 0.65) into the resin. The sample was then moved by a 3D piezostage to make 3D scans with a speed of 50 $\mu m$ s$^{-1}$ based on the pre-defined geometric design, resulting in solidified 3D microstructures, while OS was simultaneously incorporated within the polymer (FIG. 1B). After MPL fabrication, the samples were rinsed in ethanol for 1 min to remove any unsolidified resin, leaving the 3D microstructures of OS composite polymer on substrates (FIGS. 1C and 1D).

Figures 2A, 2B, 2C, 2D, 2E, 2F, 2G, 2H:
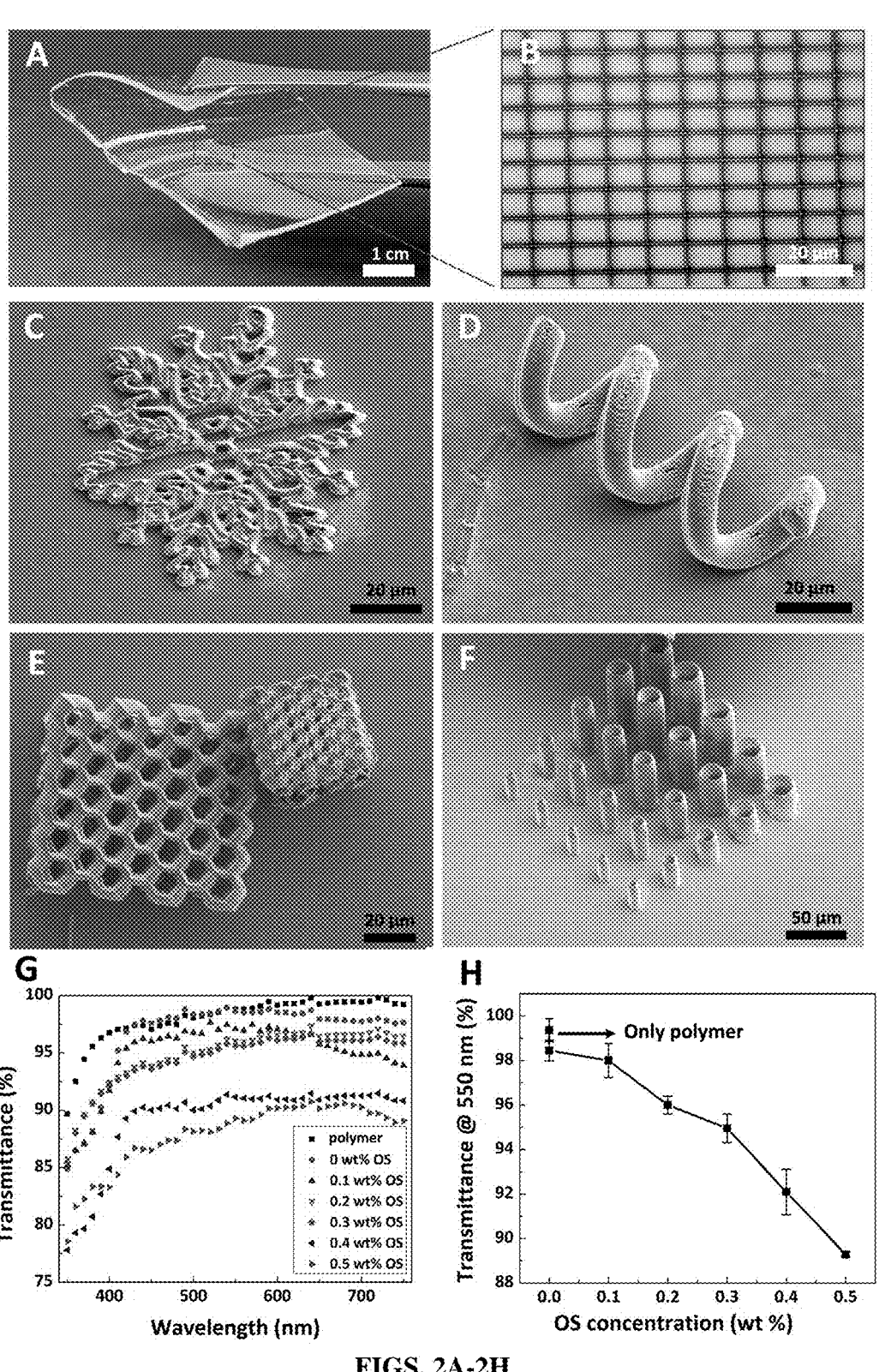
FIGS. 2A-2H: 3D microfabrication of conductive and bioactive microstructures based on OS composite resin via MPL and resin transparency.
Figures 9A, 9B, 9C, 9D:
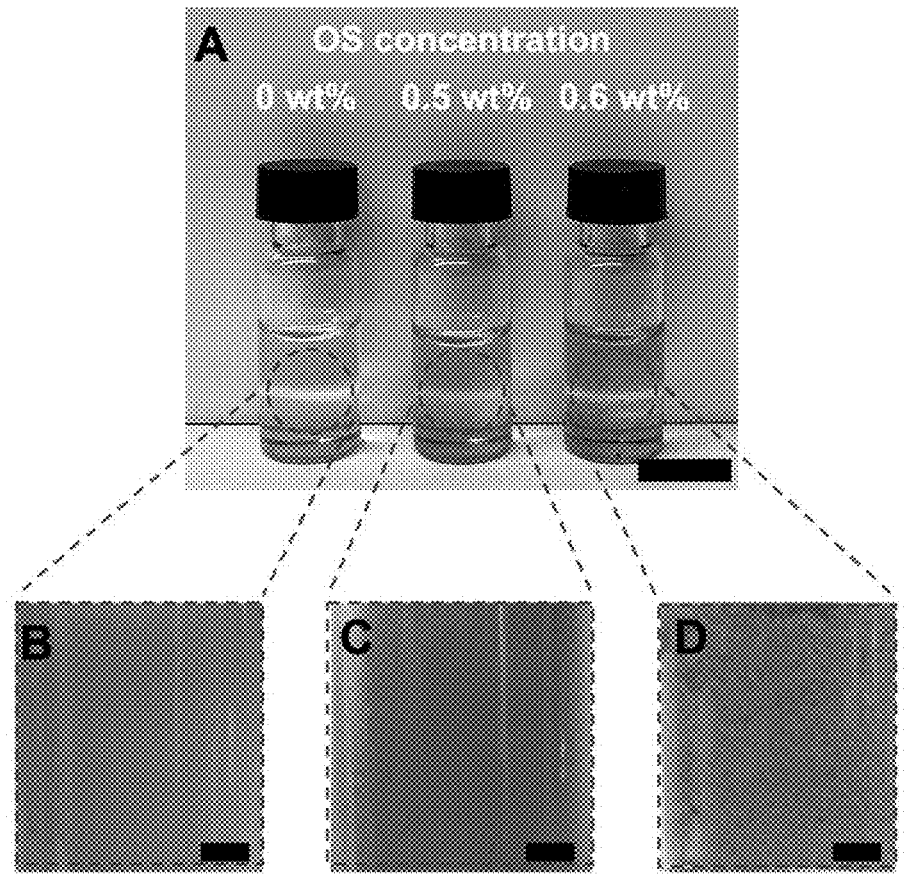
FIGS. 9A-9D: Effect of OS concentration on resin homogeneity. (Scale bar is 10 mm in (FIG. 9A and 1 mm in FIGS. 9B-D).

Resin with DMSO concentration between 25 and 35 wt % was found to be MPL-compatible. Specifically, OS was not miscible in DMSO with concentration below 25 wt %, while further addition of DMSO above 35 wt % into the resin yielded detached and lower quality microstructures (FIGS. 7B-E). The prepared resin was stable for ≈30 h at room temperature without obvious OS aggregation (FIG. 8). In addition, the maximum miscibility of OS in the resin was found to be 0.5 wt % (FIG. 9). The fabrication process was performed on either flexible polydimethylsiloxane (PDMS) (FIG. 2A) or glass substrates. FIGS. 2B-F show some examples of 3D conductive microstructures fabricated from the OS composite resin (0.5 wt % OS), including array of micro-grids, micro-snowflakes, micro-springs, micro-honeycombs, and vertical micro-tubes. It is noteworthy that the feature size (line width) of ≈400 nm was achieved when a 28 mW fs laser was focused by an oil immersion objective lens 63× (NA 1.4) and the OS composite resin was scanned with a speed of 100 μm s$^{-1}$ (FIG. 10). The optical transparency of the composite resin was characterized as a function of OS concentration (FIG. 2G). As the concentration of OS increased from 0 to 0.5 wt %, the transmittance decreased from 99% to 89% at 550 nm (FIG. 2H), demonstrating an excellent optical transparency for the composite resin. The high level of optical transmittance is an appealing feature for potential optoelectronic application of MPL-fabricated organic semiconductor composite microstructures (OSCMs).

Figures 3A, 3B, 3C, 3D, 3E, 3F, 3G, 3H, 3I, 3J, 3K, 3L:
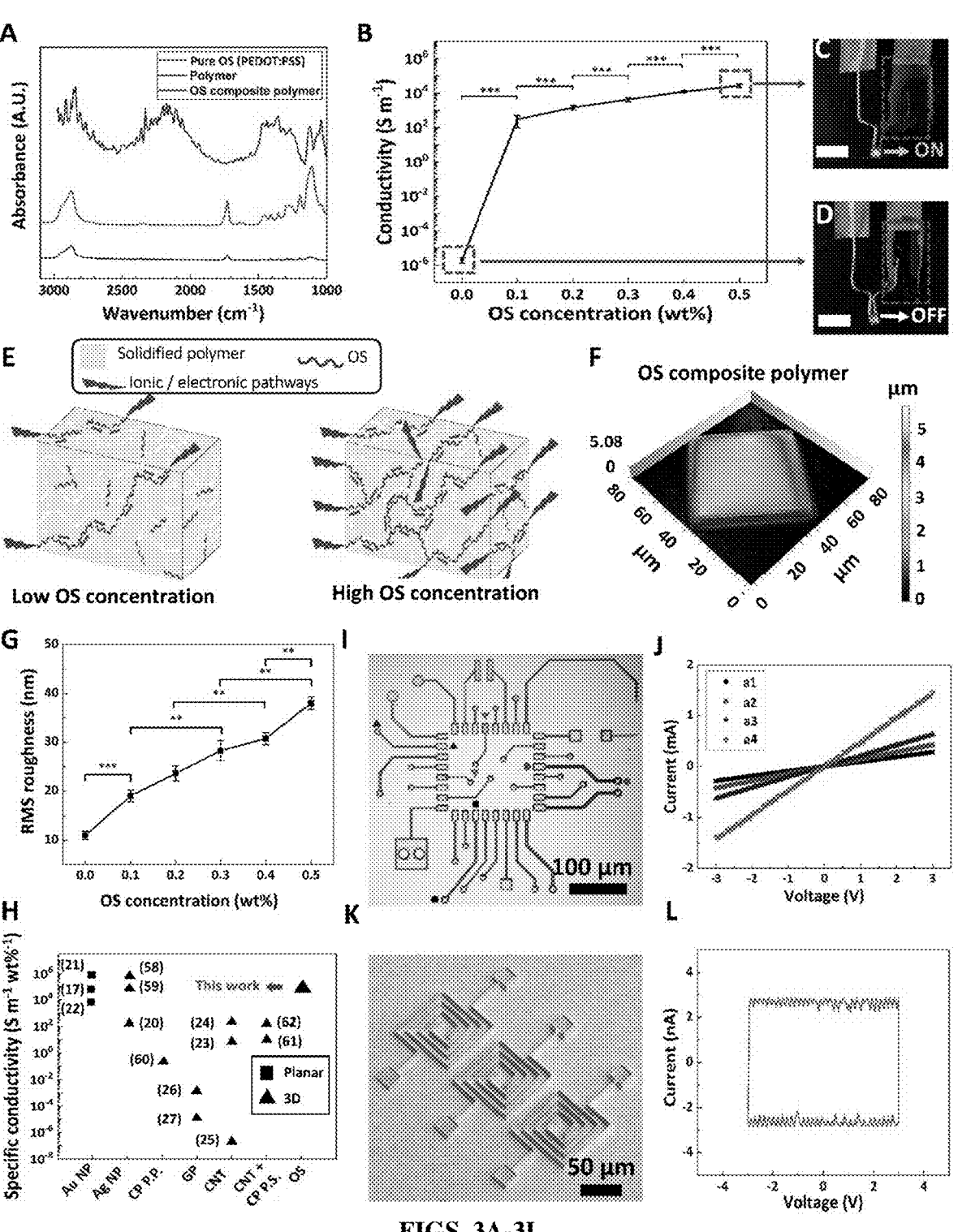
FIGS. 3A-3L: Chemical, electrical, and physical characterization of MPL-fabricated microstructures.
Figures 11A, 11B:
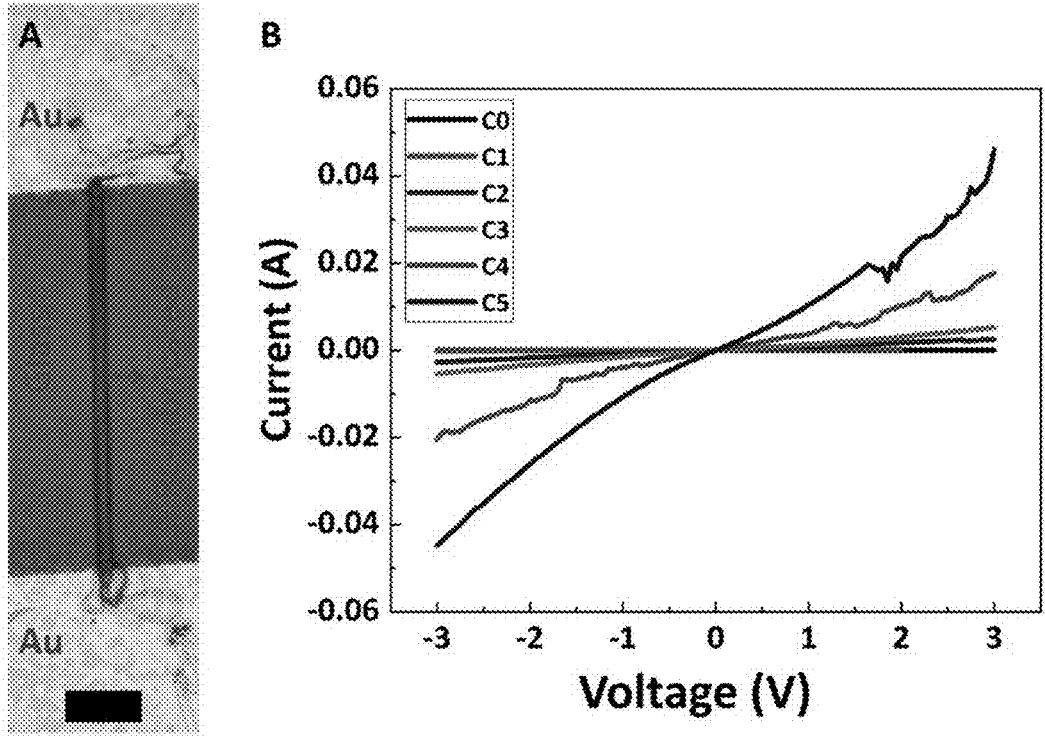
FIGS. 11A-11B: Conductivity measurement.
Figure 12:
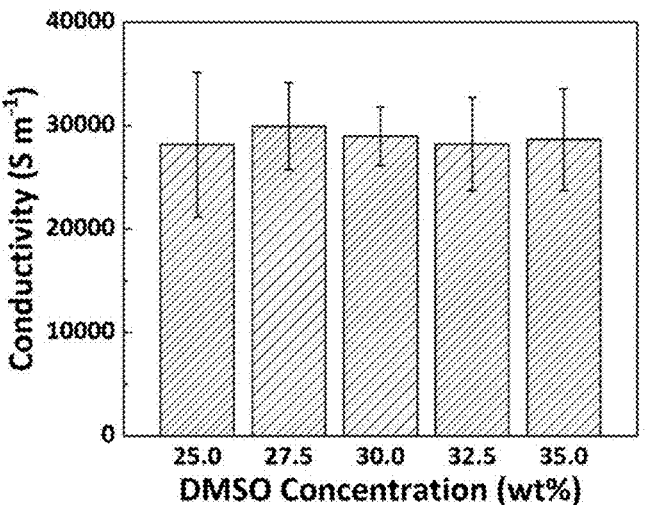
FIG. 12: Effect of DMSO concentration in the resin on electrical conductivity. Data shown as mean±SD, n=4.

Fourier transform infrared spectroscopy (FTIR) was conducted to confirm that OS was incorporated within 3D microstructures (FIG. 3A). For the OS composite polymer microstructures (shown in red curve) and polymer microstructures (shown in black curve), two characteristic peaks were observed at 2910 cm$^{-1}$ and 1724 cm$^{-1}$, which correspond to stretching of —CH and =CO bonds of the polymer, respectively. Furthermore, the OS composite polymer showed three peaks at 1162 cm$^{-1}$, 1121 cm$^{-1}$, and 1066 cm$^{-1}$ that correspond to stretching vibration of ethylenedioxy group, as well as peaks at 1345 cm$^{-1}$ and 1500 cm$^{-1}$, which can be attributed to C—C and C=C bonds in the thiophene ring of pure OS (shown in blue curve). To characterize the electrical conductivity of the OS composite polymers, bar-shaped microstructures (265 μm×10 μm×10 μm: length×width×height) were fabricated connecting two pairs of gold (Au) electrodes (FIG. 11A). A Semiconductor Device Parameter Analyzer (B1500A, Keysight) was utilized to obtain the current-voltage (I-V) curves and to calculate the electrical conductivity of the OS composite microstructures (OSCMs) (Equation 1 and FIG. 11B). FIG. 3B shows the electrical conductivity of the OSCMs as a function of different OS concentrations in the resin. As depicted, while the polymer microstructures (without OS) were not conductive, loading as low as 0.1 wt % OS into the resin dramatically increased electrical conductivity of the OSCMs over 8 orders of magnitude (from 2×10$^{-6}$±6.5×10$^{7}$ S m$^{-1}$ to 3×10$^{2}$±2×10$^{2}$ S m$^{-1}$). Furthermore, the electrical conductivity significantly increased to 2.7×10$^{4}$±6×10$^{3}$ S m$^{-1}$ by increasing the OS concentration to 0.5 wt % (the maximum miscibility concentration of OS in the resin). It is noteworthy that there was statistically significant difference in the electrical conductivities of OSCMs fabricated with 0.1, 0.2, 0.3, 0.4, and 0.5 wt % (p<0.001). To further demonstrate the electrical conductivity of the OS composite polymer compared to non-conductive polymer, OS composite polymer fabricated from a resin composed of 0.5 wt % OS with a thickness of 1 mm and conductance of less than 0.1 S was able to serve as an interconnect to switch on a light-emitting diode (FIGS. 3C and 3D). The electrical conductivity of the OS composite polymer can be attributed to presence of OS in the cross-linked polymer chains, providing both ionic and electronic conduction pathways along the polymer chains (FIG. 3E) (Ludwig et al., 2006). Moreover, the excessive increase in electrical conductivity of OSCMs is ascribed to the conductivity enhancing agent DMSO that also acts as a miscible agent. Commercially available OS PEDOT:PSS is an aqueous dispersion of chemically polymerized PEDOT in polyelectrolyte PSS with moderate electrical conductivity (ca. 100 S m$^{-1}$) (Abidian et al., 2006). It has been reported that the use of DMSO could dramatically increase the electrical conductivity of OS (about 2 orders of magnitude) (McCarthy et al., 1985;

Giannelli et al., 1997; Zhang et al., 2015), presumably due to removal of insulating counterions (i.e. PSS) from OS (Da Violante et al., 2002), reducing the columbic interactions between OS and counterions (Giannelli et al., 1997), as well as reorientation and conformation of the OS polymer chains (Whiting et al., 2011; Li, 1982). It should be noted that varying the concentration of DMSO in the resin between 25 and 35 wt % (MPL-processible range of DMSO concentration in the resin) did not significantly change conductivity (FIG. 12).

Figures 13A, 13B, 13C:
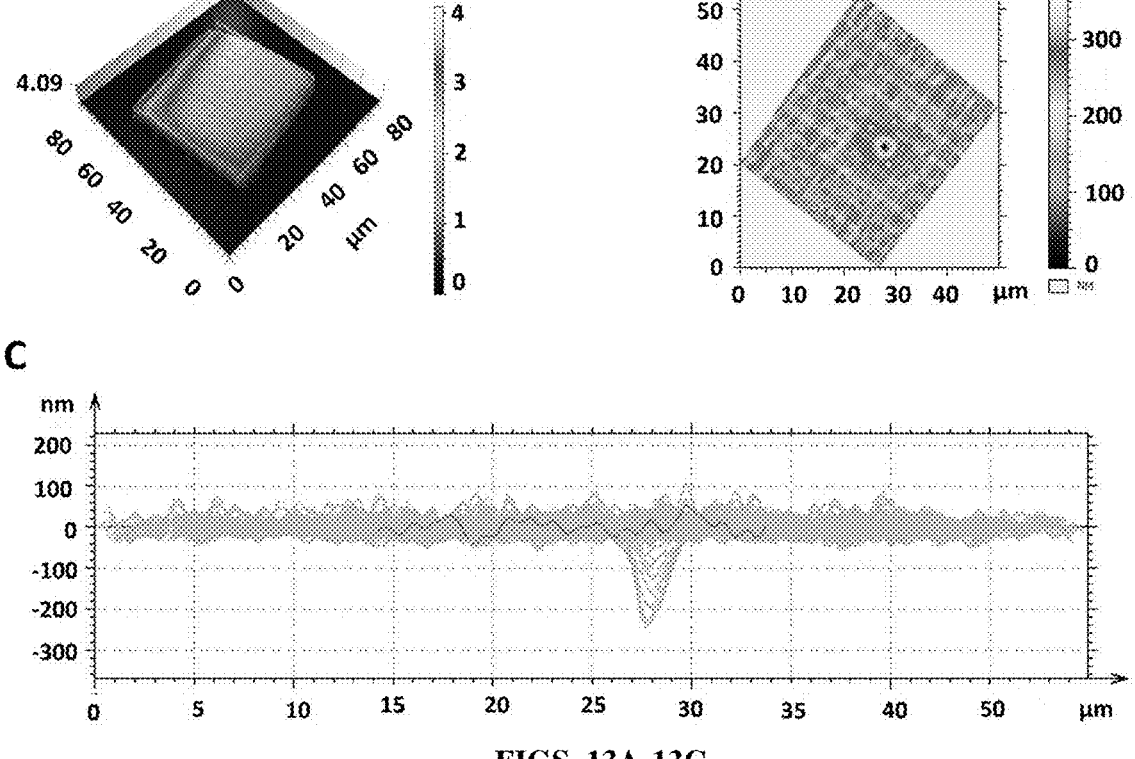
FIGS. 13A-13C: MCM of the MPL-fabricated polymer composite microcube.

Materials confocal microscopy (MCM) was utilized to assess the surface topography of the OSCMs. As previously shown in the scanning electron micrographs (FIG. 2C-F) and indicated in the 3D view of the color-coded height map (FIG. 3F), OSCMs (OS 0.5 wt %) had high-quality structural features and were relatively smooth with average surface roughness of 38 nm compared to non-conductive microstructures (FIG. 13). MCM revealed that as the OS concentration increased from 0.1 wt % to 0.5 wt %, surface roughness increased from 19±1.2 nm to 38±1.3 nm (p<0.001), respectively (FIG. 3G). Moreover, there was statistically significant difference in the surface roughness of OSCMs fabricated with 0, 0.1, 0.2, 0.3, 0.4, and 0.5 wt % OS (p<0.05). In addition to the quality of the MPL-based conductive microstructures, the specific conductivity (conductivity per concentration of conductive filler in resin) is a particularly relevant metric for evaluating the efficiency of the fabrication method, especially for large-scale fabrication at low costs (Table 1). FIG. 3H provides a comparison between the specific conductivity of the MPL-fabricated structures in relevant studies using various conductive fillers. High content metallic nanoparticles in the resin such as Au and Ag salts (10-50 wt %) demonstrated high specific electrical conductivity of MPL-based composites (10$^{4}$-10$^{6}$ S m$^{-1}$ wt %$^{-1}$), however, this method often produced planar microstructures (Carlotti & Mattoli, 2019; Nakamura et al., 2016; Shukla et al., 2011; Liu et al., 2019; Oubaha et al., 2012; Namba et al., 1998; Wang et al., 1996). In contrast, inclusion of carbon-based nanomaterials in the resin such as CNTs, graphene, and post polymerization of conductive monomers (0.01-10 wt %) yielded 3D microarchitectures with low specific conductivities (Staudinger et al., 2017; Xiong et al., 2016; Guo et al., 2012; Kurselis et al., 2013; Tao et al., 2019a; De Fazio et al., 2011; Arica et al., 1993; Gursel & Hasirci, 1992). Remarkably, the present OSCMs (0.5 wt % OS) not only exhibits high specific conductivity (≈5.4×10$^{4}$ S m$^{-1}$ wt %$^{-1}$) but also smooth surfaces and high-quality 3D structural features (FIGS. 2C-F, FIGS. 3F and 3G). The high specific conductivity together with the high-quality 3D microstructures of the present OS composite polymer represents a profound improvement in the fabrication of MPL-based 3D conductive architectures compared to previously reported composite resins (FIG. 3H).

To demonstrate the potential of MPL fabrication process based on the OS composite resin, various microelectronic devices were designed, fabricated, and characterized, including a micro-printed circuit board (μPCB), which comprises various electrical elements (FIG. 3I), and an array of microcapacitors (FIG. 3K). The straight lines in the I-V graph (FIG. 3J) showed the resistor behavior of elements a1, a2, a3, and a4 (Table 2) with conductance of 106.52±9.31, 140.16±13.14, 202.54±15.39, and 459.31±44.74 μS (n=5), respectively. FIG. 3L shows the hysteresis loop (scan rate: 2 V s$^{-1}$) of an array of microcapacitors (three microcapacitors in parallel, Table 3). The rectangular-shaped I-V curve indicates capacitor behavior with a specific capacitance of 0.08±0.02 F g$^{-1}$ (n=3) (Equation 2).

Figures 4A, 4B, 4C, 4D, 4E:
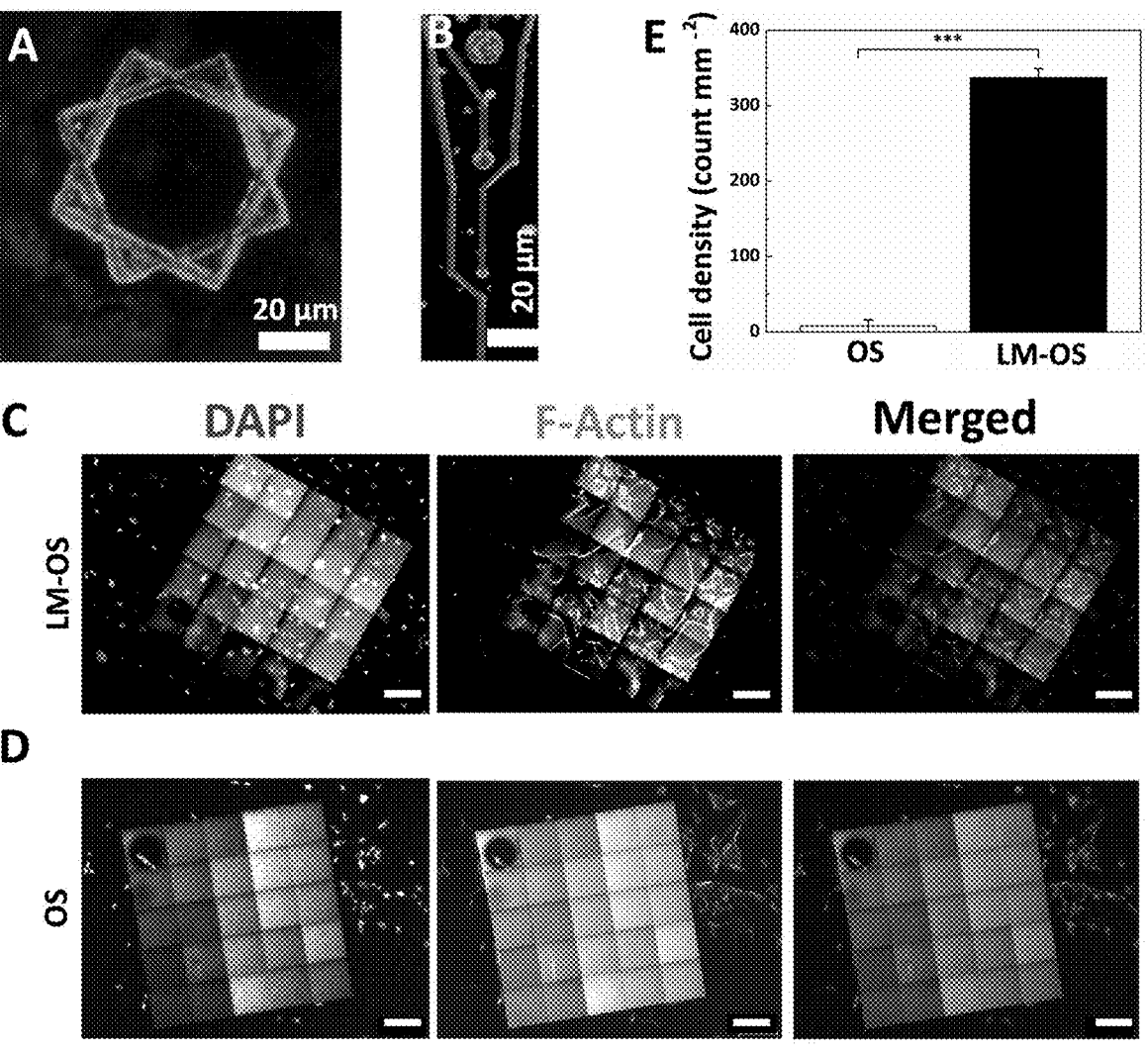
FIGS. 4A-4E: Incorporation of laminin (LM) into MPL-fabricated OSCMs.
Figure 14A:
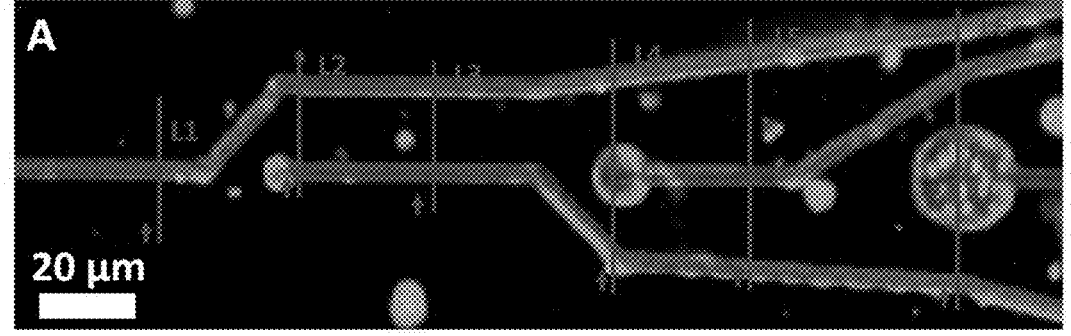
FIGS. 14A-14B: Laminin incorporation within the OS microstructure.
Figure 14B:
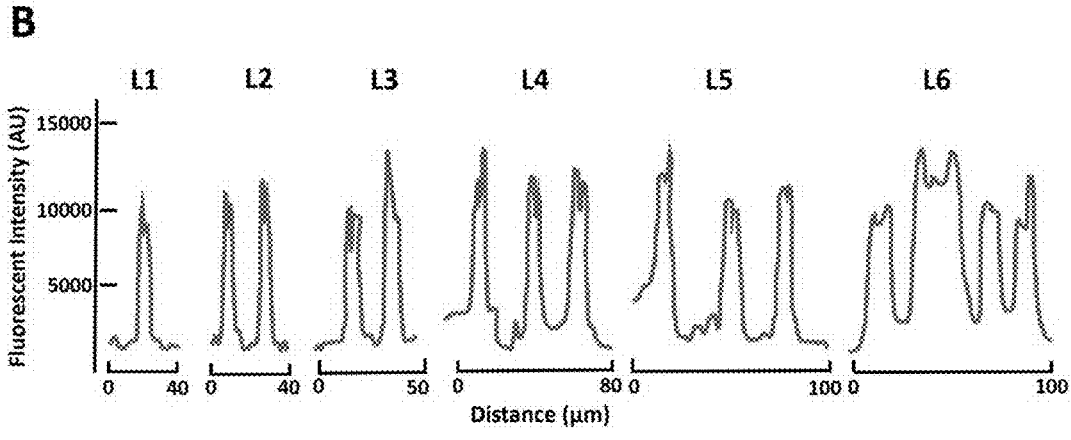

3D bioprinting of OSCMs based on MPL has potential in tissue engineering applications. To demonstrate the versatility of this method, a bioactive resin was first formulated and developed by adding laminin (LM) to the OS composite resin. LM was immobilized within OSCMs during solidification of the composite resin. Fluorescent microscopy micrographs shown in FIGS. 4A and 4B indicate the distribution and incorporation of laminin into M PL-fabricated LM-OSCMs (OS concentration in resin was 0.5 wt %, and LM concentration was 0.1 μM) and line intensity scans across the LM-OSCMs structures revealed a coefficient of variation of 5.5% (FIG. 14). Laminin is a key component of the basement membrane in multiple tissues, and is involved in structural stability, cell attachment, cell signaling, cell migration, cell proliferation as well as angiogenesis (Kros et al., 2001; Macaya et al., 2007). To confirm that the bioactivity of LM was retained throughout the entire MPL process, primary mouse endothelial cells were cultured for 48 h on the LM-OSCMs (500 μm×500 μm×2 μm: length× width×height). As shown in the fluorescent micrographs in FIGS. 4C and 4D, and demonstrated in FIG. 4E, the attachment of endothelial cells was significantly higher on LM-OSCMs compared to OS microstructures without laminin (337±20 and 8±13 cells mm$^{-2}$, respectively, p<0.001). Cells seeded on LM-OSCMs displayed evidence of adherence to substrate, proliferation, and enhanced survival, whereas the cells barely held on to the substrate and were rounded and non-proliferative on OS microstructures. These results confirmed that LM incorporated into MPL-fabricated microstructures retains its biological activity and that LM-OSCMs support and enhance the attachment, spreading, and proliferation of living cells.

OSs have been one of the most promising materials in the emerging field of bioelectronics owing to their mechanical flexibility which simulates properties of biological tissue, mixed ionic and electronic conduction that facilitates efficient biosignal transduction, and biocompatibility and facile functionalization with biomolecules for tuning biological responses (Nien et al., 2006; Piro et al., 2001; Yang et al., 2014; Kandel et al., 2000). Fabrication of organic bioelectronic devices have mostly relied on conventional lithography techniques involving photomask processes to fabricate metal electrical contacts and interconnects followed by OS electrochemical patterning (Tao et al., 2019b; Ouyang et al., 2005; Dong & Portale, 2020), impaired with their challenges and limitations. Here, a maskless method based on MPL for fabrication of bioelectronics was proposed, as schematically illustrated in FIGS. 5A-C. The proposed shape and geometry of the device is similar to Michigan style neural electrodes (Ludwig et al., 2006). The MPL fabrication process begins with construction of insulating electrode shank and base (height: 2 μm) from the polymer resin (without added OS) (schematic illustration FIG. 5A and optical micrograph representation FIG. 5G). Next, the resin was replaced with the OS composite resin (OS concentration: 0.5 wt %) and OSCMs including electrode sites (height: 7 μm, diameters: 1, 5, 10, 20, 40, and 80 μm), interconnect cables (width: 1 μm, height: 2 μm), and contact pads (length: 20 μm, width: 20 μm, height: 7 μm) were fabricated (schematic illustration FIG. 5B and optical micrograph representation FIG. 5I). Finally, the insulating layer was fabricated from the polymer resin (without added OS) to encapsulate the interconnect cables (height: 3 μm) (schematic illustration FIG. 5C and optical micrograph representation FIG. 5J). It is worth noting that the fabrication process shown in FIG. 5B can be further modified for the development of enzyme based-biosensors by first fabrication of electrode sites from OS composite resin containing biorecognition molecule such as glucose oxidase enzyme (GOx) (schematic illustration FIG. 5D and optical micrograph representation FIG. 5H), followed by construction of interconnect cables and contact pads from OS composite resin (without enzyme), (schematic illustration FIG. 5E and optical micrograph representation FIG. 5I), and finally fabrication of the insulating layer (schematic illustration FIG. 5F and optical micrograph representation FIG. 5J). FIGS. 5G-J represent optical micrographs of the fabrication steps, and FIGS. 5K and 5L show the SEM of MPL-fabricated microstructures.

Figures 6A, 6B, 6C, 6D, 6E, 6F, 6G, 6H, 6I, 6J, 6K:
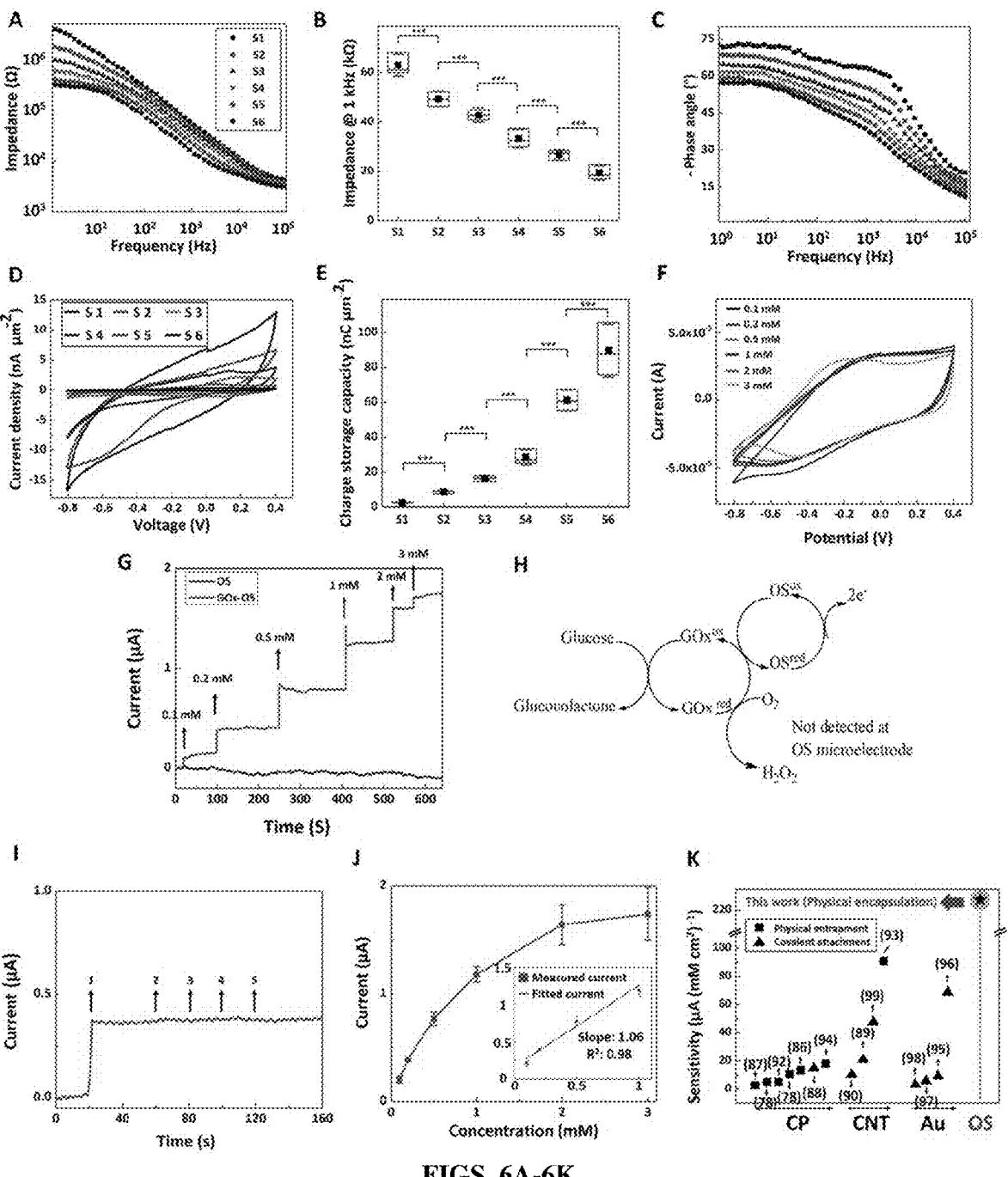
FIGS. 6A-6K: Electrochemical characterization and glucose biosensing using MPL-fabricated composite microelectrode sites.

Next, the electrochemical properties of the OS composite microelectrode sites were measured and characterized shown in the SEM micrographs in FIG. 5K using electrochemical impedance spectroscopy (EIS) and cyclic voltammetry (CV). As shown in FIG. 6A, the impedance magnitude decreased across all frequencies (1 to 10$^5$ Hz) as the diameter of the OS composite microelectrode sites increased. The larger surface area resulted in higher double layer capacitance, which is inversely related to the impedance (Antensteiner et al., 2017). Specifically, at the biologically relevant frequency of ≈1 kHz, the impedance magnitude significantly decreased from 63.13±4.56 kΩ to 19.28±3.08 kΩ (p<0.001) as the diameter of sites increased from 1 μm to 80 μm (FIG. 6B). The trend of both impedance magnitude and phase angle of the OS composite sites (FIG. 6C) were in agreement with previous studies of electrochemical patterned OS (Abidian & Martin, 2009; Abidian & Martin, 2008; Antensteiner et al., 2017). In particular, OS composite sites exhibited capacitive behavior at low frequencies (1-10 Hz) due to the dominance of double layer capacitance. However, at frequencies between 10 and 10$^3$ Hz, OS composite sites became more resistive as the frequency increased because of predominance of charge transfer reaction and diffusion associated with mixed ionic and electronic conduction of the OS (FIG. 6C) (Abidian & Martin, 2008; Antensteiner et al., 2017).

Figures 15A, 15B, 15C:
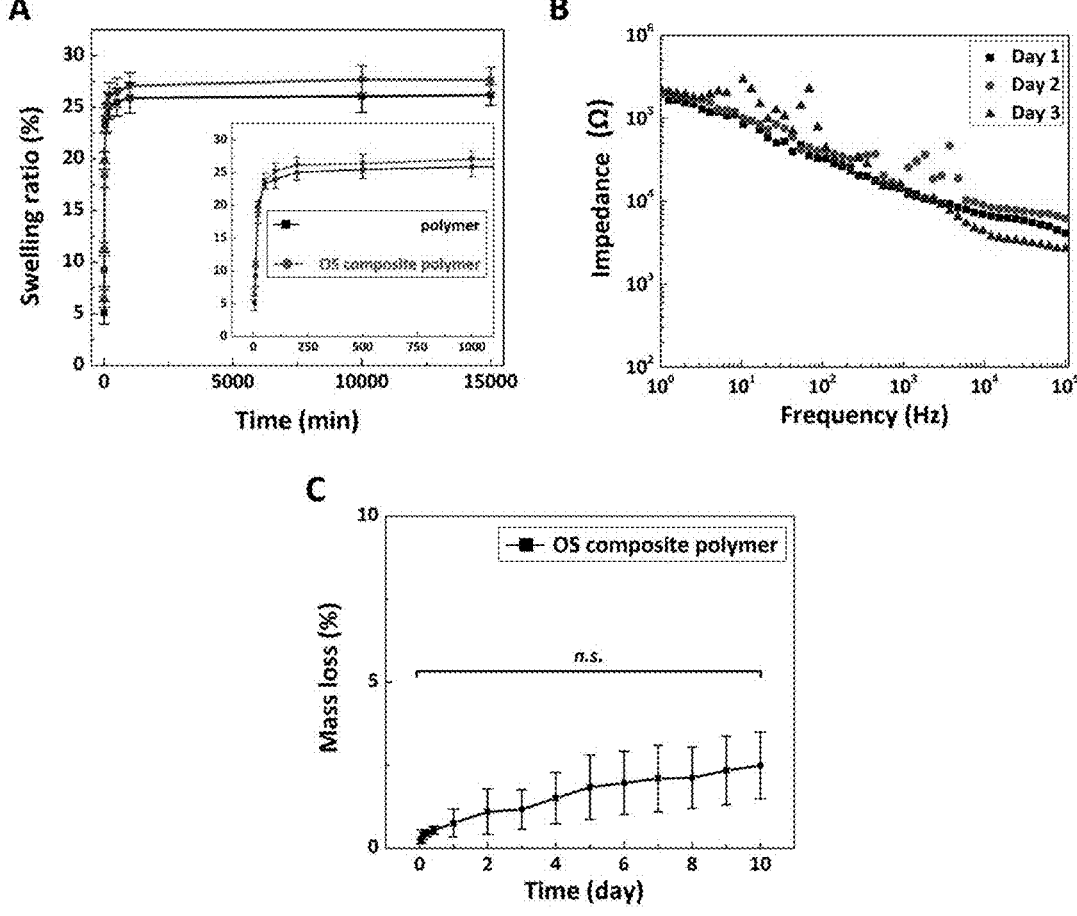
FIGS. 15A-15C: Swelling, mass loss and impedance change over time.
Figure 16:
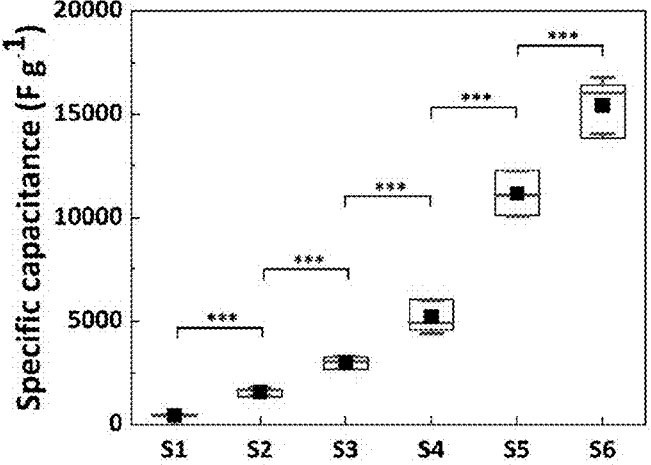
FIG. 16: Specific capacitance of OS-composite sites. Data is represented in a box graph where the black squares, red lines, and red whiskers demonstrate mean, median, and standard deviation, respectively. Data shown as mean±SD, n=3, ***p<0.001.

It has been reported that pristine OS (Zhang & Cicoira, 2017) structures and OS composite structures containing>70 wt % OS (Ghosh & Inganas, 1999; Li et al., 2020) could significantly swell in aqueous/ionic solutions. In agreement with these findings, here, adding 0.5 wt % OS did not cause a significant change in the water absorption of MPL-fabricated microstructures (FIG. 15A, no statistically significant difference between OS composite polymer and polymer) and the impedance was relatively stable in phosphate buffered saline during swelling (PBS, pH=7.4, T=37° C.) (≈7% increase at biologically relevant frequency 1 kHz after 3 days, FIG. 15B). In addition, the OS composite polymer exhibited less than ≈2.5% mass loss after 10 days (no statistically significant difference) of incubation in phosphate buffered saline (PBS, pH=7.4, T=37° C.), presumably due to hydrolysis of ester bonds (FIG. 15C). These results were in agreement with to those reported previously (Stillman et al., 2020; Zustiak & Leach, 2010). CV was conducted to study redox reactions of the OS composite sites due to ion exchange between OS and electrolyte. As shown in Equation 1, the redox reaction is accompanied by the transportation of cations inside and outside of the OS:

$$[OS^{n+}(A^-)_n] + nC^+ \underset{-e^-}{\overset{+e^-}{\rightleftarrows}} [OS^0(A^-)_n(C^+)_n], \qquad \text{(Equation 1)}$$

where OS$^+$ represents the oxidized state, OS$^0$ represents the neutral state, A$^-$ represents immobile charge balancing anions, and $C^+$ represents cations in the electrolyte. During CV, OS composite sites were swept between −0.4 V and 0.6 V at a constant scan rate of 0.1 V s⁻¹ and the cyclic I-V curves were obtained (FIG. 6D). The anodic peak potential (oxidation) was $E_{pa} \approx 0.1$ V and cathodic peak potential (reduction) was $E_{pc} \approx -0.2$ V which were in the range of previously reported OS (Abidian et al., 2006; Abidian & Martin, 2008; Antensteiner et al., 2017). As shown in FIG. 6D, the cathodic and anodic currents drastically increased as the surface area of the OS composite sites increased presumably due to increasing ion diffusion at the OS microelectrode-electrolyte interface. The charge storage capacity (CSC) is proportional to the surface area under the I-V curves and determines the charge of mobile carriers accumulated within the OS composite polymer during a I-V cycle (Equation S3). It is noteworthy that the charge storage capacity (FIG. 6E) and specific capacitance (Equation S2 and FIG. 16) significantly increased from 2.38±0.18 nC μm² to 89.73±15.14 nC μm⁻² and from 435±19 F g⁻¹ to 16398±1597 F g⁻¹, respectively (p<0.001).

Figures 17A, 17B, 17C:
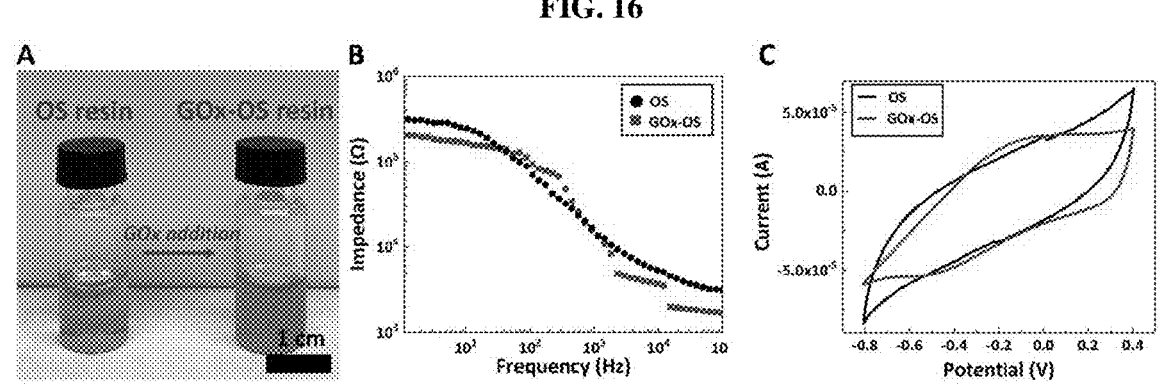
FIGS. 17A-17C: GOx-OS composite resin and electrical properties of the microelectrode.

To demonstrate the potential application of the MPL-based microstructures, a glucose biosensor was designed and fabricated as described and illustrated in FIGS. 5D-F. To date, the most commonly used amperometric glucose biosensors utilize enzyme glucose oxidase (GOx) for the specific recognition of glucose and the glucose concentration is determined by consumption of oxygen (to produce hydrogen peroxide) and oxidation of hydrogen peroxide at high potential≈+0.7V. In this study, GOx was encapsulated within the solidified OS composite microelectrodes (GOx-OS) via the MPL process from a homogeneous resin containing 0.3 mM GOx and 0.5% wt OS (FIG. 17A). EIS and CV plots of GOx-OS microelectrodes in the absence of glucose showed that the electroactivity of OS composite polymer was relatively affected by the incorporation of GOx, presumably due to excessive ion transportation that was caused by the electronegative nature of GOx (FIGS. 17B-C) (Yang et al., 2014). FIG. 6F depicts CVs of GOx-OS microelectrodes in the presence of glucose at different concentrations. Further evaluation of CSC revealed a good level of stability as its electrochemical properties showed a slight reduction (≈3%) as the glucose concentration increased from 0.1 to 3 mM. The performance of the biosensor was evaluated by measuring the currents at a pre-set polarization potential of +0.3 V vs. Ag/AgCl upon injection of increasing glucose concentration from 0.1 mM to 3 mM (red curve, FIG. 6G) in phosphate buffered saline (PBS, pH=7.4, T=37° C.), a clinically relevant concentration range for glucose in cerebrospinal fluid (Leen et al., 2012) where the glucose concentration is two thirds that of its concentration in blood (Yang et al., 2014). Various attempts have shown that OSs could be used as mediators for amperometric detection of glucose at polarization potential lower than +0.7 V (i.e. 0.3-0.4 V), presumably due to the electron pathway shown in FIG. 6H, which is an oxygen-independent detection mechanism (Kros et al., 2002; Gerard et al., 2002; Layton & Abidian, 2011). As shown in FIG. 6G, OS composite sites without encapsulated GOx (blue curve) did not show any current flow with increased glucose addition, demonstrating that the glucose detection was enzymatic. FIG. 6I shows the amperometric response of the GOx-OS biosensor to successive addition of 0.2 mM glucose (1), 0.1 mM acetaminophen (2), 0.1 mM ibuprofen (3), 0.1 mM ascorbic acid (4), and 0.1 mM urea (5). The concentration of the latter interference species in blood is typically lower than glucose, however they can produce large amperometric current compared to the glucose presumably due to their faster charge transport speed (Jung et al., 2011).

While the current response of glucose for GOx-OS composite biosensor was remarkable at potential+0.3 V, the biosensor exhibited trivial current response to other analytes (FIG. 6I), which can be attributed to elimination of oxidation effect from electrochemically active interferences at low potential of +0.3 V. These results underscore the specificity and anti-interference performance of the biosensor. The response curve of the biosensor showed an operating range of glucose concentration 0.1-3 mM (dynamic range of current response 0-2 μA), with a sensitivity of 232.9±22.5 μA mM⁻¹ cm⁻² between 0.1 and 1 mM, a limit of detection of 0.03 mM (FIG. 6J). In addition, the biosensor exhibited a response time of ≈4 s. The sensitivity of the MPL-fabricated GOx-OS microelectrodes marks a significant improvement compared to other GOx immobilization methods in the literature including physical entrapment and covalent attachment to electroactive materials (Yang et al., 2014; Macaya et al., 2007; Kros et al., 2001; Nien et al., 2006; Piro et al., 2001; Senel & Nergiz, 2012; Chen et al., 2009; Li et al., 2005; Liu et al., 2008; Setti et al., 2005; Tang et al., 2004; Jung et al., 2011; Zhang et al., 2005; Xue et al., 2006; Yang et al., 2006; Sun et al., 2007; Christwardana et al., 2017) that may suffer from inefficient enzyme loading and degradation of enzyme activity (Homaei et al., 2013; Sheldon, 2007) (FIG. 6K, Table 4).

It is worth noting that the greater sensitivity may be attributed to the efficient GOx loading by encapsulation of the enzyme within MPL-fabricated OS microelectrodes (Sheldon, 2007; Soares et al., 2006; Reetz, 1997). Furthermore, no changes in GOx activity/stability were anticipated when subjected to irradiation for ≈0.03 s by the femtosecond laser with peak power density of 141.54×10⁶ W cm⁻² (Equations S4-S9). Previous studies reported that exposure times>1 h for femtosecond lasers with peak power density of 10⁶-10¹² W cm² (Wigle et al., 2014) could cause adverse effects on the structure of DNA and proteins (damage and inactivation) (Lu et al., 2014; Botchway et al., 2010; Tsen et al., 2007). It has been reported that a femtosecond near infrared laser (peak power density≈120×10⁶ W cm²) with short exposure time (3-10 s) can be utilized for safe and efficient in vivo gene delivery and expression without any adverse effects such as apoptosis, DNA/protein degradation, and tissue damage (Zeira et al., 2003). the reproducibility (i.e. precision) of the GOx-OS biosensor was further investigated, which describes the closeness of agreement between current signals obtained using the same method but different GOx-OS biosensors. For 0.2 mM glucose injection, the mean value of the current measured by three different biosensors was 0.38 μA and the precision (relative standard deviation, RSD) was 4.02%. The Food and Drug Administration has stablished that for development of bioanalytical methods the determined precision should not exceed 15% of the RSD (Tiwari & Tiwari, 2010), therefore, the GOx-OS biosensor can be used to detect glucose with sufficient precision.

Figures 18A, 18B:
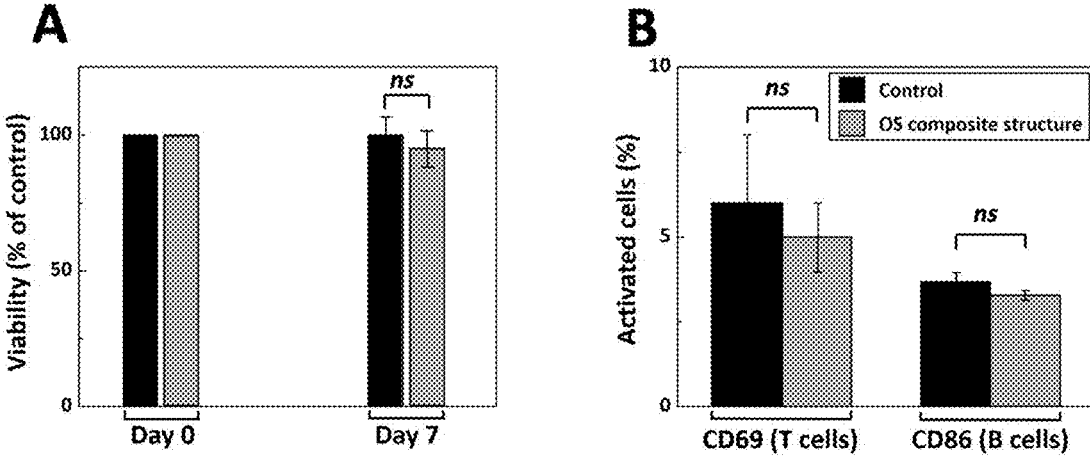
FIGS. 18A-18B: Biocompatibility assessment of OS composite structures on splenic immune cells after 7 days. Total splenic cells from a mouse were cultured for 7 days on OSCM or control structures.

The biocompatibility of the OS composite structures was evaluated by culturing lymphocytes, namely splenic T-cells and B-cells, on the fabricated surfaces and compared them with control surfaces (without OS composite structures), with respect to viability and expression of activation markers of the cells by flow cytometry, after 7 days of culture. OS composite polymers did not induce cell mortality with approximately 94% cell viability compared to the control surfaces (no statistically significant difference) (FIG. 18A).

Figures 19A, 19B:
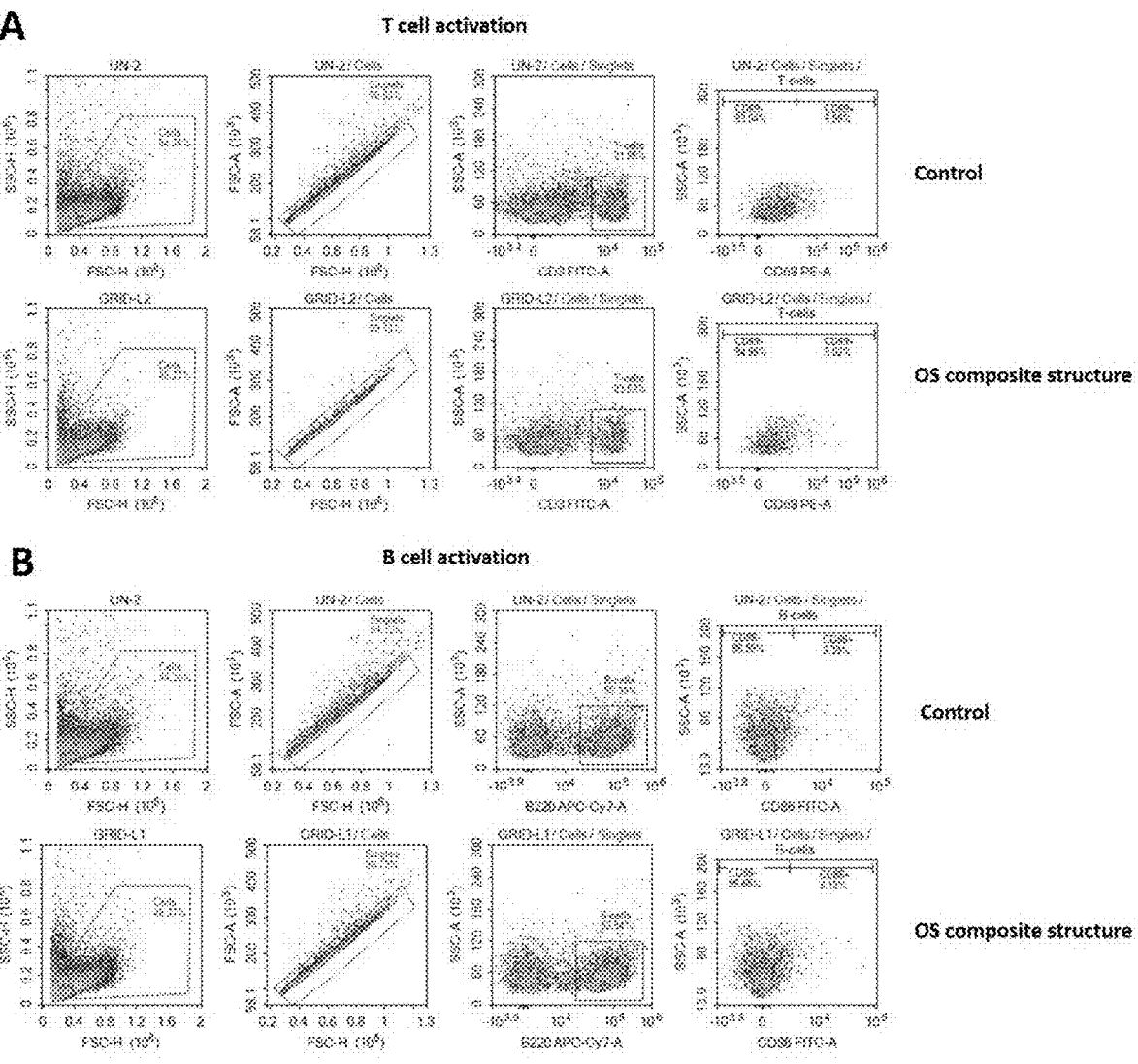
FIGS. 19A-19B: Flow cytometry analysis of splenic lymphocytes for biocompatibility assessment. Total splenic cells from a mouse were cultured for 7 days on OSCM or control structures. After gating splenic cells from a healthy mouse and using a side scatter (SSC) vs forward scatter (FSC) plot to exclude debris, doublets and clumps, single cells were gated using FSC-A vs FSC-H plot. The singlets were then characterized by fluorophore conjugated antibodies. T-cells are identified by positive staining for the T-cell marker CD3, and the gated T-cells were explored for the surface expression of CD69 which is a marker for activated T-cells (FIG. 19A). Similarly, B-cells were identified by positive staining for B220 and the gated B-cells were analyzed for the expression of CD86, which is a marker for activated B-cells (FIG. 19B). Note: no activating triggers were deliberately added to these cultures; the intent was to see if the fabricated structures can themselves activate the lymphocytes.
Figures 20A, 20B, 20C, 20D, 20E, 20F, 20G:
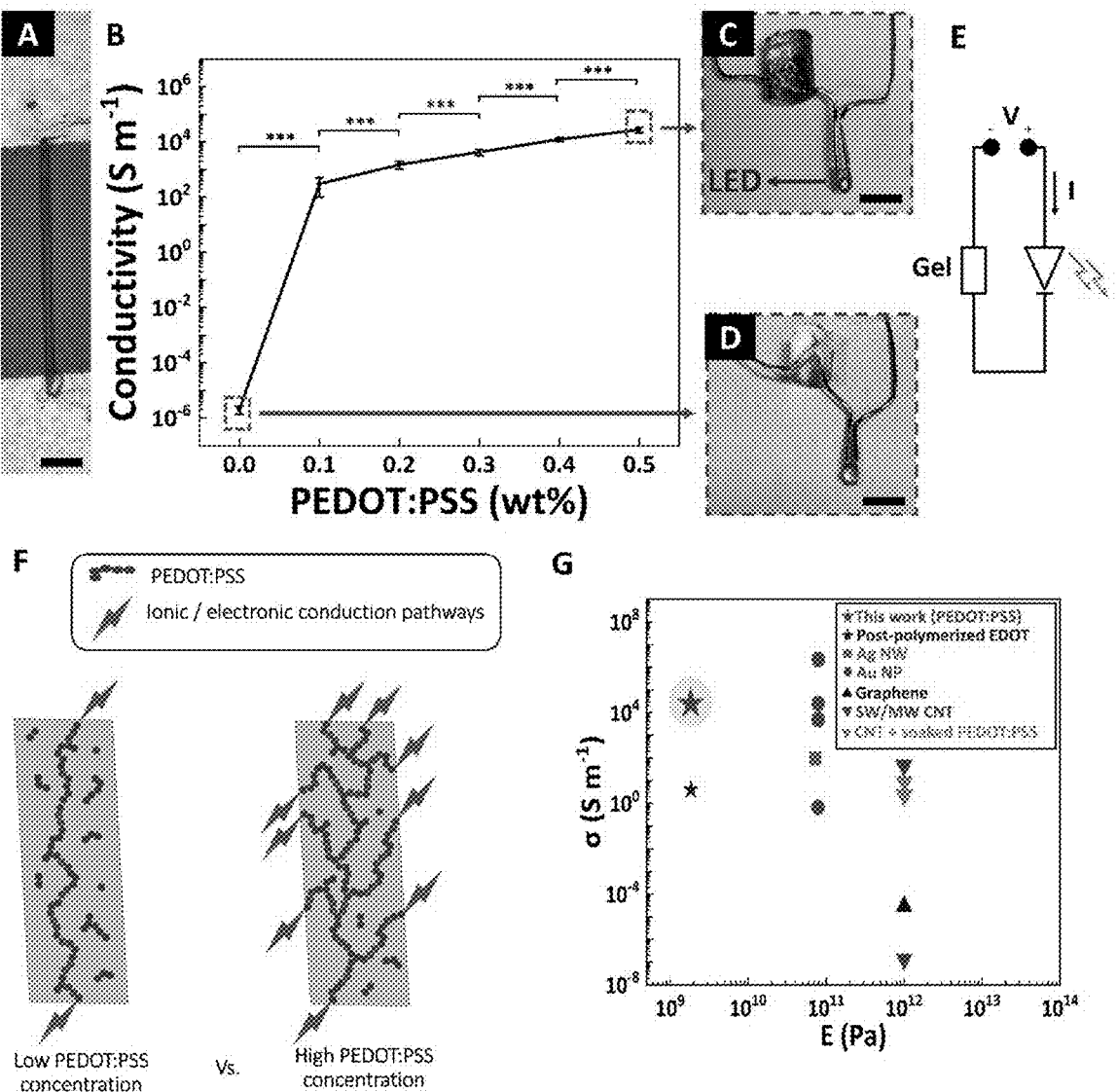
FIGS. 20A-20G: Electrical and mechanical characterization of TPP-fabricated structures.
Figures 21A, 21B, 21C, 21D, 21E, 21F:
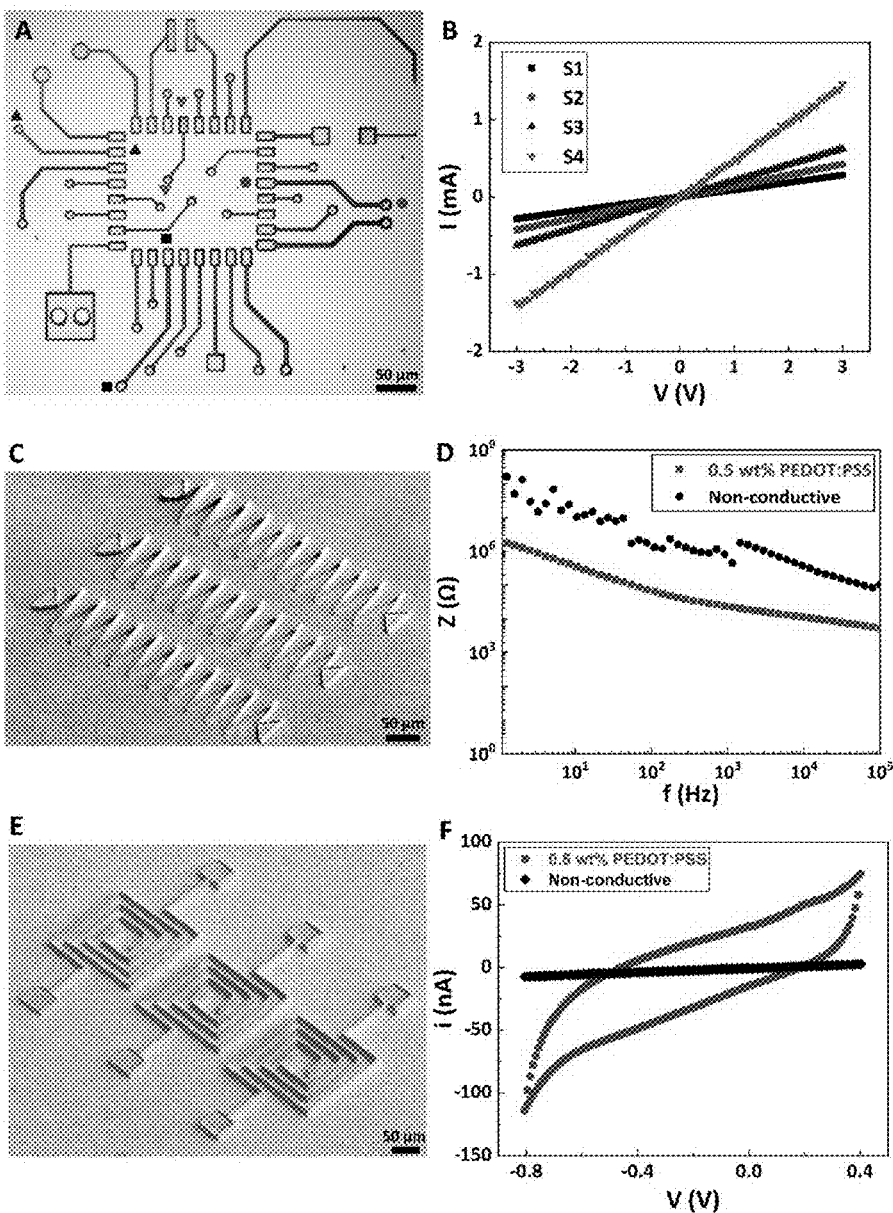
FIGS. 21A-21F: Fabrication and characterization of microelectronic devices.
Figures 22A, 22B, 22C, 22D, 22E, 22F, 22G, 22H:
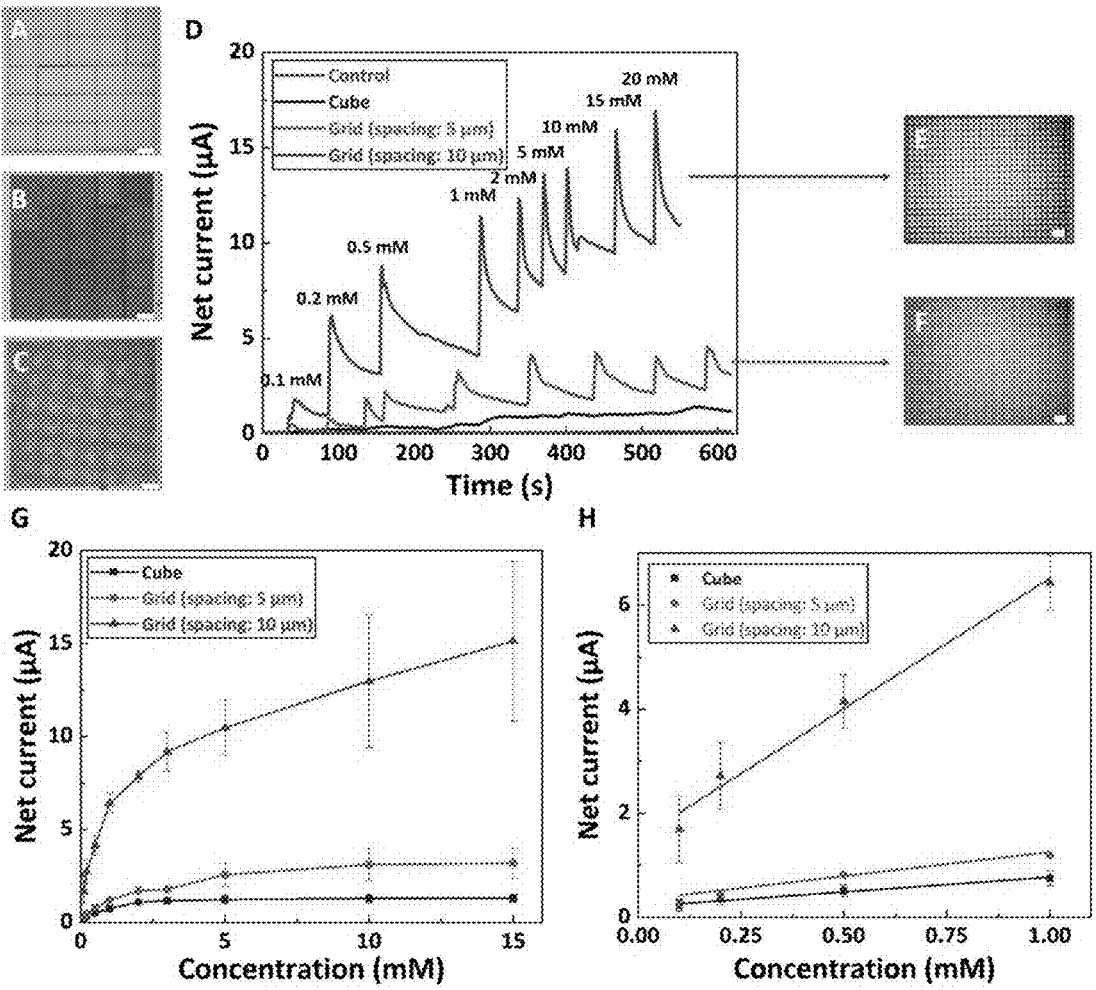
FIGS. 22A-22H: TPP-fabricated biosensors for amperometric detection of glucose.
Figures 23A, 23B, 23C, 23D, 23E, 23F, 23G:
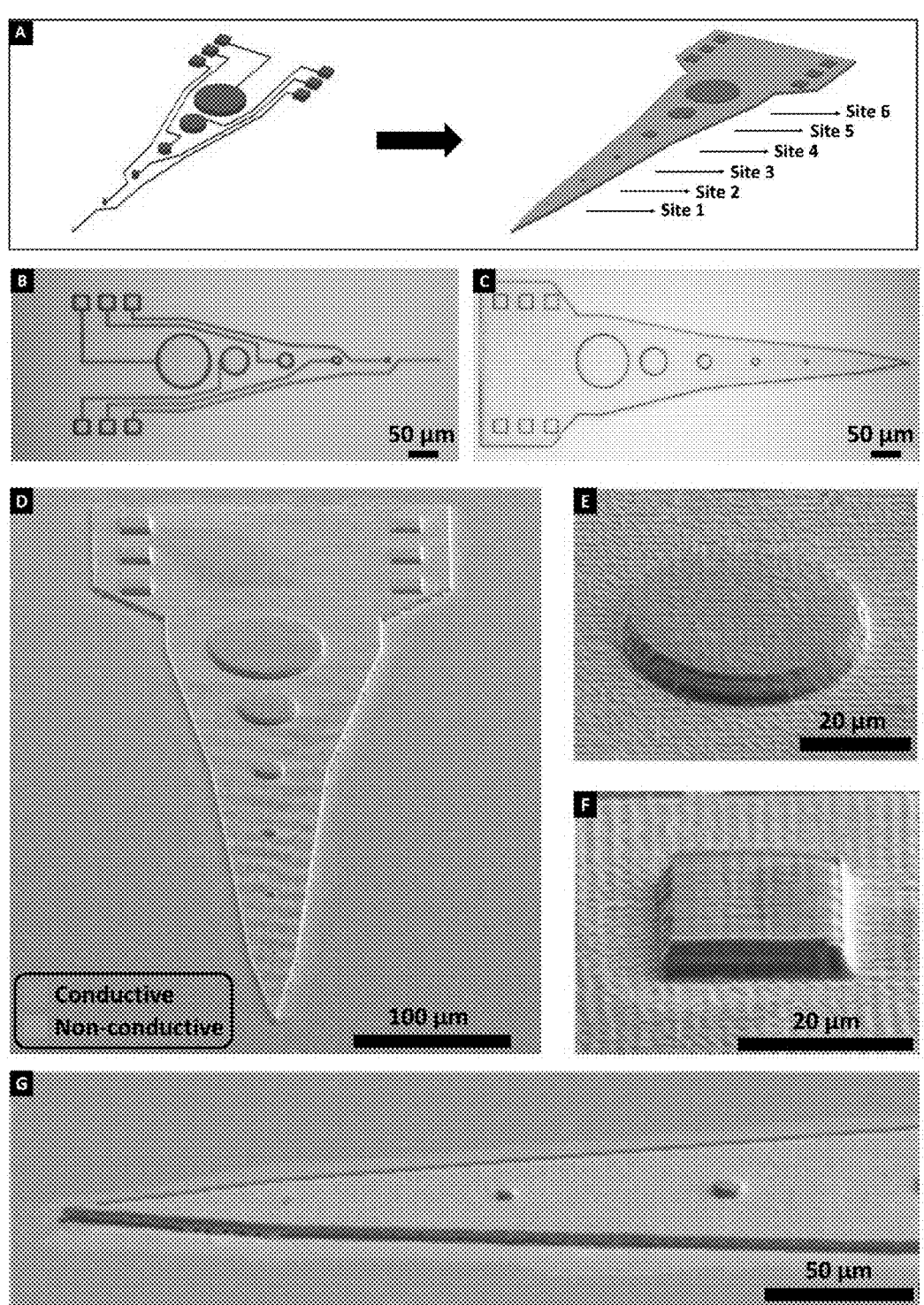
FIGS. 23A-23G: Fabrication of hybrid Michigan-style microelectrode via TPP.

Potential effect of OS composite polymers on cell activation was also studied. Expression of CD69 (activation marker for T-cells) and CD86 (activation marker for B-cells) were analyzed by flow cytometry (FIG. 18B and FIG. 19). After 7 days of culture, there was no significant difference in the expression of activation markers on the lymphocytes between OS composite structures and control surfaces. Together, these results demonstrate that a 7-day incubation of primary T-cells and B-cells with OS composite polymer did not induce cell mortality or cell activation. These findings support the biocompatibility of OSCMs with primary mammalian cells, allowing these cells to survive, without any untoward inhibitory or stimulatory effects, thus supporting their use in biomedical applications.

Effect of DMSO Concentration in the Resin on MPL-fabricated Microstructures. As shown in FIG. 7A, OS would aggregate in the resin without DMSO, which demonstrates its vital role in preparation of homogeneous resin for MPL. Microstructures fabricated from OS composite resins with $$\sigma = \frac{GA}{l}, \qquad \text{(Equation S1)}$$

where $\sigma$ is electrical conductivity (S m$^{-1}$), G is electrical conductance (S) and is derived from the slope of I-V curve, A is the cross-section area of the microstructure (10 μm×10 μm) and l is the length of the microstructure (265 μm).

Effect of DMSO concentration on Electrical Conductivity. Effect of DMSO concentration on conductivity of MPL-fabricated microstructures was investigated. In the range of MPL-processible DMSO concentration (25-35 wt %), the conductivity was measured to be 2.8×10$^4$±7×10$^3$, 2.9×10$^4$±4.2×10$^3$, 2.8×10$^4$±2.8×10$^3$, 2.8×10$^4$±4.5×10$^3$, and 2.8×10$^4$±4.9×10$^3$S m$^{-1}$ for resins with DMSO concentration of 25, 27.5, 30, 32.5, and 35 wt %, respectively. As shown, varying DMSO concentration in the resin (containing 0.5 wt % OS) in the range of 25-35 wt % did not significantly change the electrical conductivity of MPL-fabricated microstructures.

TABLE 1

Specific electrical conductivity of MPL-fabricated microstructures in the literature.

| Conductive Agent | Concentration (wt %) | Resin | Specific conductivity (S m$^{-1}$ wt %$^{-1}$) | Reference |
|---|---|---|---|---|
| CNT | 0.01 | Femtobond 4B | 7 | 23 |
| CNT | 0.2 | Acrylic-thiol | $2.3 \times 10^2$ | 24 |
| Graphene | ≈0.02 | Silicon/Zirconium | $1.4 \times 10^{-3}$ | 26 |
| EDOT | ≈20 | PEGA | $2 \times 10^{-1}$ | 60 |
| HAuCl$_4$ | 30 | SU-8 | $8.3 \times 10^5$ | 21 |
| Ag nanowires | 0.4 | Thiol-acrylate | $2.3 \times 10^2$ | 20 |
| MWCNT-doped resin + PEDOT:PSS In situ self-assembly | 0.32 | Acrylamide | $1.41 \times 10^2$ | 62 |
| MWCNT-doped resin + PEDOT Interpenetration | 0.25 | PEGA | 8.9 | 61 |
| CNT | 5 | Ormocers b59 | $1.94 \times 10^{-7}$ | 25 |
| HAuCl$_4$ | ≈1.87 | SU-8 | $9.2 \times 10^3$ | 22 |
| HAuCl$_4$ | 50 | PEG-triacry (annealing) | $4.4 \times 10^4$ | 17 |
| Graphene | 10 | N/A | 9.85E−06 | 27 |
| AgNO$_3$ | 7.3 | PVP Polyvinylpyrolidone | $3.9 \times 10^5$ | 59 |
| AgBF$_4$ | 0.2 | PVK polyvinylcarbazole | $1.5 \times 10^6$ | 58 |

DMSO concentrations higher than 35 wt % did not have mechanical integrity and tend to detach from the substrate (FIGS. 7B-D). While the OS composite resin with DMSO concentration range between 25 wt % and 35 wt % was printable (FIG. 7E), the OS composite resins were not MPL-compatible with DMSO concentrations higher than 45 wt %.

Effect of OS Content on conductivity of MPL-Fabricated Microstructures. To measure the electrical conductivity, first, a partially Au-coated coverslip was fabricated. Resins with various OS concentrations were prepared (i.e. 0 wt % (C0), 0.1 wt % (C1), 0.2 wt % (C2), 0.3 wt % (C3), 0.4 wt % (C4), and 0.5 wt % (C5)). Bar-shaped microstructures connected two gold-coated parts via MPL process (FIG. S5A). Current-voltage (I-V) measurement was performed (FIG. 11B), and electrical conductivity was calculated based on the following equation:

TABLE 2

Length of resistor elements (lines) in the micro-printed circuit board. All lines have thickness and width of 2 μm and 1 μm, respectively. Length of the elements was measured using ZENPro software.

| Element | Modeled Length (μm) | Measured length (μm) |
|---|---|---|
| a1 | 180 | 180.02 |
| a2 | 155 | 155.16 |
| a3 | 130 | 129.21 |
| a4 | 70 | 70.01 |

TABLE 3

| | Dimensions of the microcapacitor. Length, width, and height of the elements were measured using ZENPro software. | | | | | |
|---|---|---|---|---|---|---|
| Element | Modeled Length (μm) | Measured Length (μm) | Modeled Width (μm) | Measured Width (μm) | Modeled Height (μm) | Measured Height (μm) |
| Cubic pad | 20 | 20.03 | 20 | 20.03 | 2 | 2.05 |
| Cable (one side) | 430 | 430.53 | 1 | 1.12 | 2 | 2.03 |

Calculation of Specific Capacitance. Specific capacitance ($C_{SP}$) of the OS-composite microstructures was calculated using the following equation:

$$C_{sp} = \frac{1}{2\Delta V v m} \int_{V_1}^{V_2} i dV,$$ (S2)

where v is scan rate (0.1 V s$^{-1}$), A is surface area, m is the mass of the microstructures, and $\Delta V$ is the potential sweep window. Mass of the microcapacitors was calculated based on the density of OS-composite resin ($\rho$=1.14 pg μm$^{-3}$).

Laminin incorporation within the microstructures. To investigate the immobilization of laminin within the microstructures, line scans were created at various locations and fluorescent intensity of laminin was measured (FIGS. 16A and 16B). The results showed that in LM-OSCMs, the fluorescent intensity was 10345±573 AU with coefficient of variance of 5.5% (n=14, mean±SD).

Calculation of Charge Storage Capacity. The charge storage capacity (Q) of the OS-composite microstructures was calculated based on the following equation:

$$Q = \frac{1}{vA} \int_{V_1}^{V_2} i dV,$$ (S3)

where v is scan rate (0.1 V s$^{-1}$), A is surface area, and AV is the potential window ($\Delta V$=1.2 V). GOx-OS composite resin and electrical properties of GOx-OS composite microelectrodes. As shown in FIG. 17A, addition of GOx to OS resin (with a light blue color due to presence of OS), gives a yellow hue to the GOx-OS composite resin. Impedance spectrum (FIG. 17B) and cyclic voltammetry (FIG. 17C) were compared between OS composite and GOx-OS composite microelectrode sites with diameter of 80 μm.

TABLE 4

| | Sensitivity of the developed glucose biosensors. | | |
|---|---|---|---|
| Material | Method | Sensitivity (μA cm$^{-2}$ mM$^{-1}$) | Reference |
| CP PEDOT:PSS nanofibers | Physical entrapment | 6.4 | 78 |
| CP PEDOT:PSS nanofibers | Physical entrapment | 9.2 | 78 |
| CP PEDOT | Physical entrapment | 12.4 | 86 |
| CP PEDOT film | Physical entrapment | 2.7 | 87 |
| CP Ppy/propylic acid | Covalent attachment | 13.4 | 88 |
| CP PEDOT | Physical entrapment | 14.1 | 94 |

TABLE 4-continued

| | Sensitivity of the developed glucose biosensors. | | |
|---|---|---|---|
| Material | Method | Sensitivity (μA cm$^{-2}$ mM$^{-1}$) | Reference |
| CP PEDOT:PSS | Physical entrapment | 6.43 | 92 |
| CNT | Covalent attachment | 20.6 | 89 |
| CNT | Covalent attachment | 11.3 | 90 |
| CNT | Covalent attachment | 47.8 | 99 |
| CNT | Physical entrapment | 91 | 93 |
| Gold Au nanoparticles | Covalent attachment | 8.8 | 95 |
| Gold Chitosan - Au nanoparticles | Covalent attachment | 69.3 | 96 |
| Gold Au nano particle | Covalent attachment | 5.7 | 97 |
| Gold Au nano particle | Covalent attachment | 3.8 | 98 |

Femtosecond Laser Specifications. Two-photon polymerization laser (Mai Tai™ DeepSee, MTEV HP 1040 S, Spectra Physics) was utilized to fabricate microstructures. The spot size of the laser ($\theta$) was calculated to be 1.5 μm based on the following formula:

$$\theta = 1.22 \frac{\lambda}{N.A.},$$ (S4)

where $\lambda$ is the laser wavelength (780 nm), and N.A. is the numerical aperture (0.65) of the 40× objective (Plan N, OLYMPUS).

Energy of pulse (E) was measured to be 2.5×10$^{-10}$ J from this equation:

$$E = \frac{p}{f},$$ (S5)

where p is average laser power (20 mW) and f is repetition rate of the laser beam (80 MHz).

Peak power (PP) was calculated to be 2.5 W from the following equation:

$$PP = \frac{E}{\omega},$$ (S6)

where $\omega$ is laser pulse width (100 fs).

Energy density ($\sigma$) of the laser beam was measured to be 0.014 J cm$^{-2}$ using the following formula:

$$\sigma = \frac{E}{A},$$ (S7)

where A is the area of the spot size ($\pi\theta^2/4$).

Power density ($\phi$) of the laser beam was calculated to be 141.54 MW cm$^{-2}$ using the following equation:

$$\rho = \frac{PP}{A}$$ (S8)

To calculate the exposure time of resin to laser beam (t) was calculated to be 0.03 s by using the following equation:

$$t = \frac{\theta}{v}, \qquad (S9)$$

where v is fabrication velocity (50 μm s$^{-1}$), and θ is the spot size (1.5 μm).

Figures 24A, 24B:
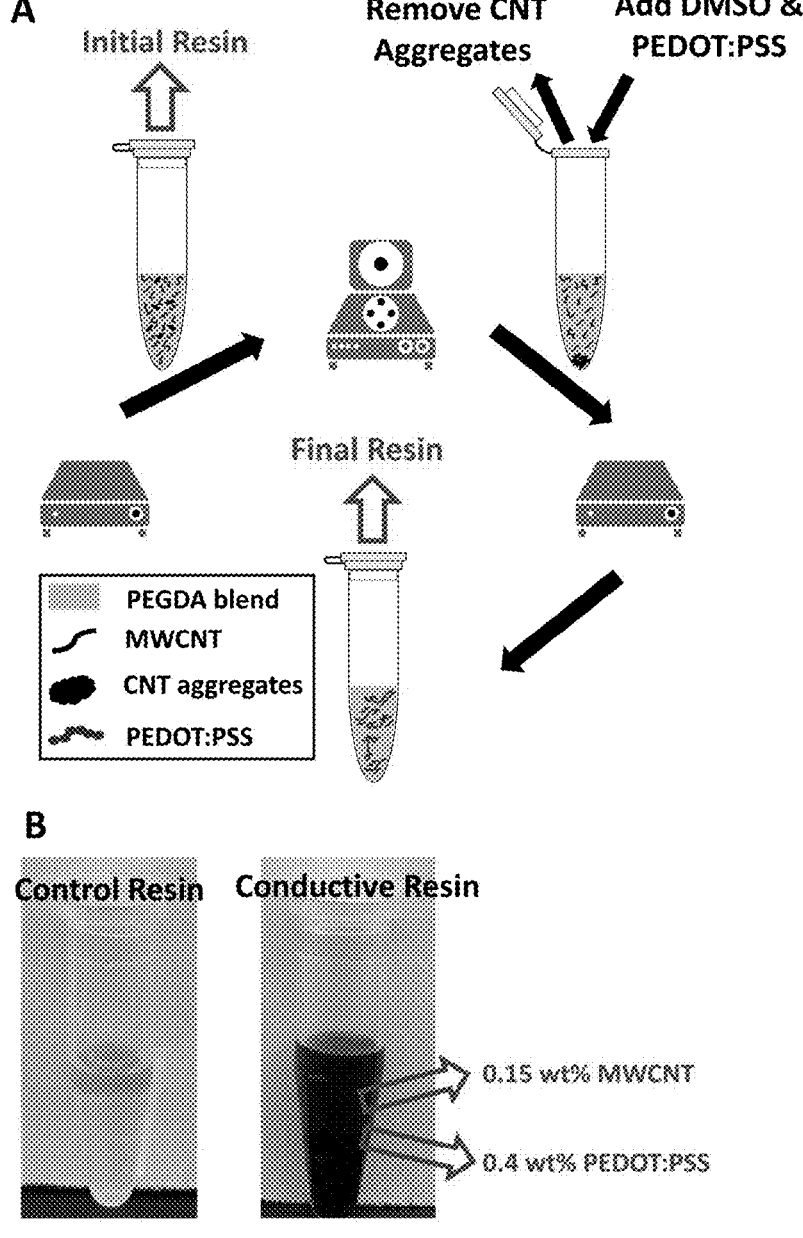
FIGS. 24A-24B: Ink preparation.

For PEDOT:PSS/MWCNT—doped composite resin, preparation consisted of two main steps (FIG. 24A). First, a mixture of MWCNTs, pentaerythritol tetrakis(3-mercapto-propionate) (PETMP), T-POL, and PEGDA was magnetically stirred for 12 h. To maximize the incorporation concentration acid-purified MWCNTs (3.86 wt % content of carboxyl groups) with short length (10-30 μm were used PETMP was used to disperse MWCNTs in PEGDA blend. The branched thiol groups in PETMP interacted with functionalized carboxyl groups in MWCNTs, making them miscible in PEGDA matrix. Following 12 h stirring, MWCNT aggregates were removed from the mixture through centrifugation. In the second step, dimethyl sulfoxide (DMSO) and (PEDOT:PSS) were added to the ink, which was then stirred for 2 h. The reason for adding DMSO was to maximize the solubility of PEDOT:PSS in the ink through hydrogen bonding between sulfonic acid groups in PSS and SO groups in DMSO. The final resin was therefore composed of two carbon-based conductive fillers, i.e. MWCNTs and PEDOT:PSS, in a highly homogenized PEGDA-based composite (FIG. 24B). MWCNTs needed at least 10 h of stirring to become homogenized in the resin by dissolving in PETMP. In contrast, PEDOT:PSS became miscible in the resin within 2 h through addition of DMSO, and prolonged stirring resulted in formation of aggregated PEDOT:PSS particles. Hence, in the case of adding all elements together, by the time MWCNTs were homogenized, PEDOT:PSS was aggregated and removed from the mixture via centrifugation, thus a two-step strategy was used for ink preparation.

Figures 25A, 25B, 25C, 25D, 25E, 25F, 25G:
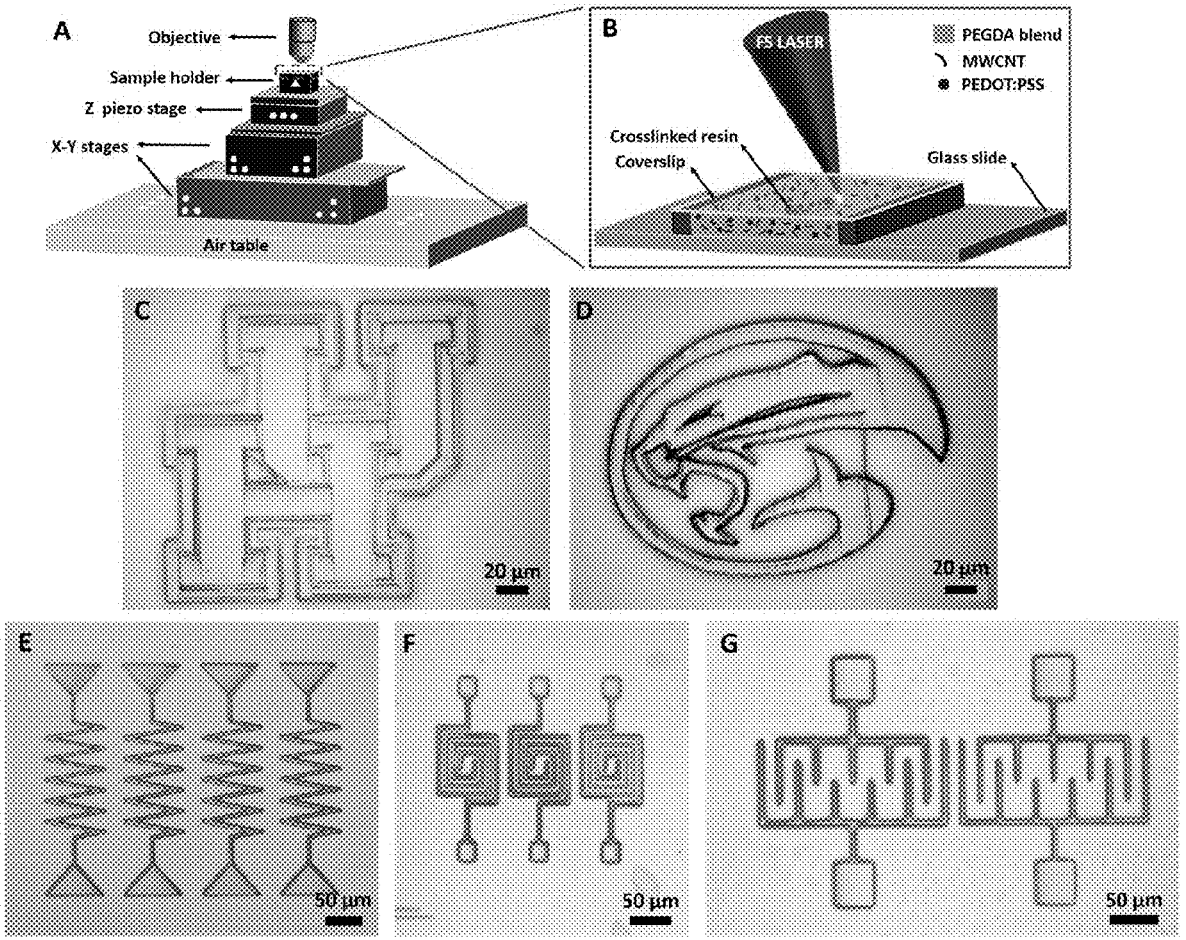
FIGS. 25A-25G: TPP fabrication.
Figures 26A, 26B, 26C, 26D, 26E:
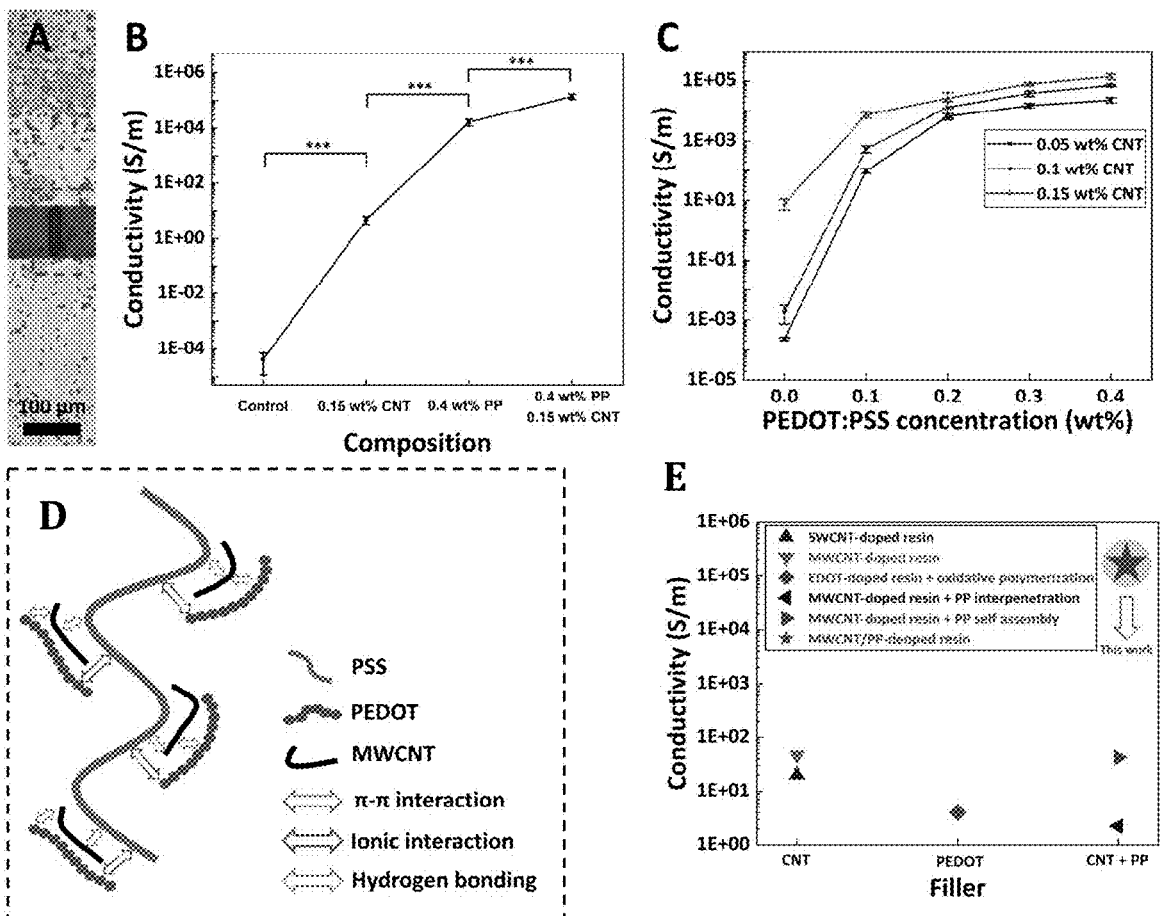
FIGS. 26A-26E: Electrical characterization of TPP-fabricated microstructures.

Next, the developed resin was fabricated into conductive microstructures via TPP (FIG. 9). Direct laser printing via TPP lithography is extremely sensitive to the resin formulation and homogeneity. Presence of two miscible solvents, i.e. PETMP for MWCNTs and DMSO for PEDOT:PSS, led to formation of a highly homogenized resin. Moreover, centrifugation of the resin removed large MWCNT aggregates, which would otherwise cause local heating, resin burning, and structural deformations. FIG. 25A illustrates a schematic of the experimental setup, including computer-controlled motorized stages, sample holder, and the laser objective, which were all located on an air table. During TPP fabrication, femtosecond laser beams crosslinked the ink at the focused region through three-order nonlinear absorption. 3D microstructures were generated up-side-down on the upper coverslip by laser scanning based on computer-designed 3D route (FIG. 25B). FIGS. 26C and 26D display University of Houston (UH) logo and cougar symbol, respectively. Electronic microdevices were also constructed, including an array of resistors (FIG. 25E), common capacitors (FIG. 25F), and micro integrated capacitors (FIG. 25G). These results demonstrate that the homogenized ink can be utilized to prepare high-resolution and well-defined microstructures for a wide range of scientific and industrial applications, including chip-scale electronics, microactuators, and bioelectronic microdevices.

To investigate the electrical properties of the microstructures based on PEDOT:PSS/MWCNT-doped ink, first microbars (length: 125 μm, width: 20 μm, and height: 5 μm) were designed and fabricated which connected two parts of a gold-coated glass (FIG. 26A), followed by current— voltage (I-V) measurements. Electrical conductivity was measured in four different ink compositions: control (without MWCNTs (CNT) and PEDOT:PSS (PP)), 0.15 wt % CNTs, 0.4 wt % PP, and 0.4 wt % PP+0.15 wt % CNT (FIG. 26B). It was observed that presence of 0.15 wt % MWCNTs and 0.4 wt % PEDOT:PSS in the ink resulted in outstanding improvement in electrical conductivity over 10 orders of magnitude, i.e. from 4.15E-05±3.01E-04 S m$^{-1}$ to 140050±29414 S m$^{-1}$ (n=5). FIG. 26C displays the electrical conductivity of microstructures with respect to various contents of MWCNTs (0.05, 0.1, and 0.15 wt %) and PEDOT:PSS (0, 0.1, 0.2, 0.3, and 0.4 wt %) in the ink. Without PEDOT:PSS, addition of 0.05 wt %, 0.1 wt %, and 0.15 wt % MWCNTs to the resin yield the conductivity value of 0.000233±0.000289 S m$^{-1}$, 0.00193±0.00193 S m$^{-1}$, and 8±3.137 S m$^{-1}$, respectively (n=5). At higher MWCNT concentrations, excess amount would aggregate and be removed from the system through centrifugation. Moreover, at 0.15 wt % MWCNTs, conductivity was 7425±1560.2 S m$^{-1}$, 26612.5±14512.41 S m$^{-1}$, 79500±, and 140050±29414 S m$^{-1}$ by incorporation of 0.1, 0.2, 0.3, and 0.4 wt % PEDOT:PSS to the resin, respectively (n=5). 0.4 wt % was found to be the maximum concentration for PEDOT:PSS since at higher contents, non-homogenous particles would aggregate shortly after addition of PEDOT:PSS and DMSO to the composite resin. It is noteworthy that it was shown that incorporation of 0.5 wt % PEDOT:PSS in a PEDGDA-based resin improved the electrical conductivity of TPP-fabricated microstructures up to 27000 S m$^{-1}$.

Here, it was demonstrated that the formulation of PEDOT:PSS and MWCNTs in the ink leads to almost one order of magnitude increase in electrical conductivity. The microstructures based on the PEDOT:PSS/MWCNT-doped ink, π-π interactions between PEDOT and MWCNTs, as well as hydrogen bonding between PSS and MWCNTs may lead to formation of conductive complexes (FIG. 26D). The significant enhancement in conductivity is therefore due to higher electron transfer density and more delocalized charge on both PEDOT and MWCNT. As it can be seen in FIG. 26E, the obtained electrical conductivity based on PEDOT:PSS/MWCNT-doped resin in this work is considerably higher than comparable studies.

Figures 27A, 27B, 27C, 27D:
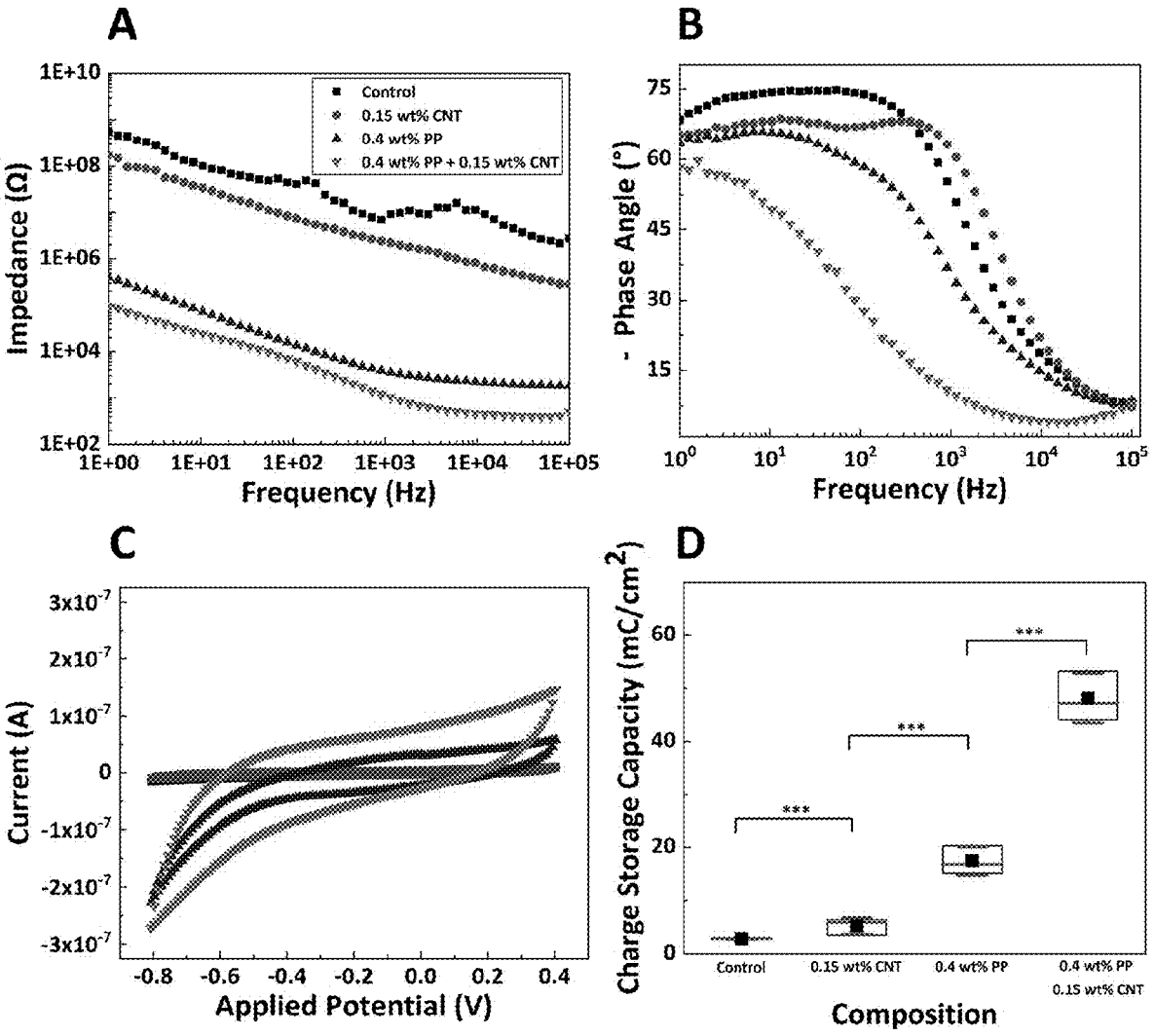
FIGS. 27A-27D: Electrochemical analysis of cubic sites.

To evaluate the electrochemical behavior, cubic sites were fabricated with dimensions of 50 μm×50 μm×2 μm (length×width×height) using various ink formulations, then electrochemical impedance spectroscopy (EIS) and cyclic voltammetry (CV) were carried out (FIG. 27). EIS revealed that over the entire frequency spectrum (1-10$^5$ kHz), the impedance of cubic sites in all compositions decreased with increasing frequencies, however, the presence of both PEDOT:PSS and MWCNTs in the composite ink led to significant reduction in impedance typically by almost 3 orders of magnitude compared to control sites (FIG. 27A). For example, at the biologically relevant frequency of 910 Hz, the impedance dramatically dropped from 4322.85±2367.84 kΩ (control composition) to 1458.152±812.73 kΩ (at 0.15 wt % MWCNTs) and 33.46±7.44 (at 0.4 wt % PEDOT:PSS). Cubic sites exhibited even lower impedance, i.e. 18.28±5.58 kΩ (n=3, p<0.001), upon addition of both PEDOT:PSS (0.4 wt %) and MWCNTs (0.15 wt %), which can be explained by formation of conductive complexes between MWCNTs and PEDOT:PSS in the microstructures. These results demonstrated that TPP-fabricated microstructures based on PEDOT:PSS/MWCNTs-doped ink are promising for biomedical applications such as neural recording and stimulation, in which low-impedance electrode-tissue interface is essential. Phase angle plot of the impedance spectrum (FIG. 27B) also showed that both control and MWCNT-doped sites were more capacitive as opposed to resistive in a wide range of frequency spectrum (<10 kHz). PEDOT:PSS-incorporated sites showed a dramatic phase angle decrease, but still remained capacitive-dominated in frequencies<1 kHz. In the case of PEDOT:PSS/MWCNT-incorporated sites however, the shift from capacitive to resistive properties occurred at a much lower frequency, i.e. =100 Hz, and the sites were almost purely resistive at frequencies>1 kHz (=10°). In other words, cubic sites based on PEDOT:PSS/MWCNT-doped resin act as capacitors in frequency range of 1-100 Hz and as resistors for frequencies>100 Hz for neural recording and stimulation applications. CV was used to explore the capacity of charge storage density of TPP-fabricated sites, in which the potential of working electrode was swept in the window of –0.8 V to 0.4 V with a scan rate of 100 mV s$^{-1}$ (FIG. 27C). The integrated surface area of CV graphs is proportional to the charge storage capacity (CSC). As shown in FIG. 27D, CSC increased from 2.81±0.05 mC cm$^{-2}$ in control composition to 5.27±1.56 mC cm$^{-2}$ upon addition of 0.15 wt % MWCNT to the ink (n=3, p<0.001). However, presence of PEDOT:PSS (0.4 wt %) resulted in over three fold increase in CSC to 17.4±2.65 mC cm$^{-2}$ (n=3, p<0.001). More importantly, incorporation of both PEDOT: PSS (0.4 wt %) and MWCNTs (0.15 wt %) in the ink further enhanced the CSC to 48.13±4.67 mC cm$^{-2}$ (n=3, p<0.001). In other words, cubic sites based on PEDOT:PSS/MWCNT-doped ink increase the CSC by ≈1600% compared to control samples.

In summary, the inventors have formulated a homogeneous and transparent MPL compatible resin-doped with an OS to fabricate 3D OS composite microstructures with enhanced electrical conductivity. Using MPL process, various microelectronic elements and devices were fabricated on glass and PDMS substrates, including micro-resistors, micro-capacitors and µPCBs. It was demonstrated that laminin can be incorporated into these OS composite polymers without a significant loss of activity as the resultant structures were able to support cellular adhesion and growth. The above-mentioned MPL process was extended to fabricate enzyme-based biosensors, and incorporated GOx into the microstructures and demonstrated that glucose can be detected with high sensitivity, specificity, and reproducibility. The presented MPL-compatible OS composite resins can be used for the production of soft, bioactive, and conductive microstructures for various applications in the emerging fields of flexible bioelectronics/biosensors, nanoelectronics, organ-on-chips, and immune cell therapies.

For the first time, the inventors demonstrated that direct incorporation of 0.5 wt % PEDOT:PSS in the ink significantly improves the conductivity of 3D microstructures over 10 orders of magnitude, and presence of laminin protein enhances the cellular attachment to the TPP-fabricated microstructures. The inventors also showed fabrication procedure and electrical characterization of printed circuit boards and hybrid neural microelectrodes.

Furthermore, the inventors successfully demonstrated that direct incorporation of 0.4 wt % PEDOT:PSS and 0.15 wt % MWCNT in a PEGDA-based ink improved the electrical conductivity of TPP-fabricated microstructures over 10 orders of magnitude up to 140000 S m$^{-1}$. Electrochemical analysis revealed that microstructures based on the formulated ink exhibit low impedance and high charge storage capacity. These bioactive and conductive 3D microdevices can be hugely employed in various applications ranging from flexible microelectronics to biomedical engineering.

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

VI. REFERENCES

The following references, to the extent that they provide exemplary procedural or other details supplementary to those set forth herein, are specifically incorporated herein by reference.

Abidian et al., "Conducting-polymer nanotubes for controlled drug release," vol. 18, no. 4, pp. 405-409, 2006.

Abidian et al., "Interfacing conducting polymer nanotubes with the central nervous system: chronic neural recording using poly (3, 4-ethylenedioxythiophene) nanotubes," vol. 21, no. 37, pp. 3764-3770, 2009.

Abidian et al., "Conducting-polymer nanotubes improve electrical properties, mechanical adhesion, neural attachment, and neurite outgrowth of neural electrodes," vol. 6, no. 3, pp. 421-429, 2010.

Abidian & Martin, "Experimental and theoretical characterization of implantable neural microelectrodes modified with conducting polymer nanotubes," *Biomaterials*, vol. 29, no. 9, pp. 1273-1283, 2008.

Abidian & Martin, "Multifunctional nanobiomaterials for neural interfaces," *Advanced Functional Materials*, vol. 19, no. 4, pp. 573-585, 2009.

Agarwala et al., "Development of bendable strain sensor with embedded microchannels using 3D printing," vol. 263, pp. 593-599, 2017.

Antensteiner et al., "Conducting polymer microcups for organic bioelectronics and drug delivery applications," *Adv. Mater.* vol. 29, no. 39, p. 1702576, 2017.

Arica et al., "Immobilization of glucose oxidase: a comparison of entrapment and covalent bonding," vol. 58, no. 3, pp. 287-292, 1993.

Bogue, "Recent developments in MEMS sensors: A review of applications, markets and technologies," 2013.

Botchway et al., *Mutat. Res. Rev. Mutat. Res.* 2010, 704, 38.

Carlotti & Mattoli, "Functional Materials for Two-Photon Polymerization in Microfabrication," vol. 15, no. 40, p. 1902687, 2019.

Carlsson et al., "Laminin and fibronectin in cell adhesion: enhanced adhesion of cells from regenerating liver to laminin," vol. 78, no. 4, pp. 2403-2406, 1981.

Chen et al., *Carbon* 2009, 47, 3106.

Christwardana et al., *Korean J. Chem. Eng.* 2017, 34, 2916.

Coleman et al., "Percolation-dominated conductivity in a conjugated-polymer-carbon-nanotube composite," vol. 58, no. 12, p. R7492, 1998.

Da Violante et al., "Evaluation of the cytotoxicity effect of dimethyl sulfoxide (DMSO) on Caco2/TC7 colon tumor cell cultures," vol. 25, no. 12, pp. 1600-1603, 2002.

De Fazio et al., "Alterations in cerebral oxidative metabo-
lism following traumatic brain injury," vol. 14, no. 1, pp.
91-96, 2011.
Dong & Portale, "Role of the Processing Solvent on the
Electrical Conductivity of PEDOT:PSS," vol. 7, no. 18, p.
2000641, 2020.
Gerard et al., Biosens. Bioelectron. 2002, 17, 345.
Ghosh & Inganas, Adv. Mater. 1999, 11, 1214.
Giannelli et al., "Induction of cell migration by matrix
metalloprotease-2 cleavage of laminin-5," vol. 277, no.
5323, pp. 225-228, 1997.
Green & Abidian, "Conducting polymers for neural pros-
thetic and neural interface applications," vol. 27, no. 46,
pp. 7620-7637, 2015.
Guimard et al., "Conducting polymers in biomedical engi-
neering," vol. 32, no. 8-9, pp. 876-921, 2007.
Guo et al., "Using laser microfabrication to write conductive
polymer/SWNTs nanocomposites," vol. 7, no. 1, p. 44,
2012.
Gürsel & Hasirci, "Matrix entrapment of glucose oxidase by
7 irradiation," vol. 13, no. 3, pp. 150-155, 1992.
Homaei et al., J. Chem. Biol. 2013, 6, 185.
Jang, "Conducting polymer nanomaterials and their appli-
cations," in Emissive Materials Nanomaterials: Springer,
2006, pp. 189-260.
Jayne et al., "Dynamic Actuation of Soft 3D Micromechani-
cal Structures Using Micro-Electromechanical Systems,"
vol. 3, no. 3, p. 1700293, 2018.
Jung et al., J. Electrochem. Sci. Technol 2011, 2, 124.
Kabessa et al., "3D Nanophotonic Structures Constructed in
a Curved Space Inspired by General Relativity Concepts,"
in Integrated Photonics Research, Silicon and Nanopho-
tonics, 2016, p. ITulA. 7: Optical Society of America.
Kandel et al., Principles of neural science. McGraw-hill
New York, 2000.
Kawata et al., "Finer features for functional microdevices,"
vol. 412, no. 6848, pp. 697-698, 2001.
Kros et al., "Poly (3, 4-ethylenedioxythiophene)-based glu-
cose biosensors," Adv. Mater vol. 13, no. 20, pp. 1555-
1557, 2001.
Kros et al., Adv. Mater. 2002, 14, 1779.
Kurselis et al., "3D fabrication of all-polymer conductive
microstructures by two photon polymerization," vol. 21,
no. 25, pp. 31029-31035, 2013.
Layton & Abidian, "Conducting Polymer Nanofiber-Based
Biosensor for Detection of Neurochemicals", presented at
5th International IEEE Engineering-in-Medicine-and-Bi-
ology-Society (EMBS) Conference on Neural Engineering
(NER), Cancun, MEXICO, Apr. 27-May 1, 2011.
Leen et al., Plos One 2012, 7, 42745.
Li et al., Anal. Bioanal. Chem. 2005, 383, 918.
Li et al., "Achieving λ/20 resolution by one-color initiation
and deactivation of polymerization," vol. 324, no. 5929,
pp. 910-913, 2009.
Li et al., Adv. Funct. Mater. 2020, 30, 1.
Liu et al., Biosens. Bioelectron. 2008, 23, 1887.
Liu et al., "Precise assembly and joining of silver nanowires
in three dimensions for highly conductive composite
structures," vol. 1, no. 2, p. 025001, 2019.
Long et al., "Recent advances in synthesis, physical prop-
erties and applications of conducting polymer nanotubes
and nanofibers," vol. 36, no. 10, pp. 1415-1442, 2011.
Lu et al., J. Phys. D: Appl. Phys. 2014, 47, 315402.
Ludwig et al., "Chronic neural recordings using silicon
microelectrode arrays electrochemically deposited with a
poly (3, 4-ethylenedioxythiophene)(PEDOT) film," vol.
3, no. 1, p. 59, 2006.
Macaya et al., "Simple glucose sensors with micromolar
sensitivity based on organic electrochemical transistors,"
Sens. Actuat. B-Chem. vol. 123, no. 1, pp. 374-378, 2007.
Malliaras & Abidian, "Organic bioelectronic materials and
devices," vol. 27, no. 46, p. 7492, 2015.
Masui et al., "Laser fabrication of Au nanorod aggregates
microstructures assisted by two-photon polymerization,"
vol. 19, no. 23, pp. 22786-22796, 2011.
McCarthy et al., "The role of cell adhesion proteins—
laminin and fibronectin—in the movement of malignant
and metastatic cells," vol. 4, no. 2, pp. 125-152, 1985.
Nakamura et al., "Fabrication of gold microstructures using
negative photoresists doped with gold ions through two-
photon excitation," vol. 18, no. 25, pp. 17024-17028,
2016.
Namba et al., "Glucose and methionine uptake by rat brain
tumor treated with prodrug-activated gene therapy," vol.
25, no. 3, pp. 247-250, 1998.
Nien et al., Electroanalysis "Amperometric glucose biosen-
sor based on entrapment of glucose oxidase in a poly (3,
4-ethylenedioxythiophene) film," vol. 18, no. 13-14, pp.
1408-1415, 2006.
Niesler & Hermatschweiler, "Two-Photon Polymeriza-
tion—A Versatile Microfabrication Tool: From maskless
lithography to 3D printing," vol. 12, no. 3, pp. 44-47,
2015.
Oubaha et al., "Graphene-doped photo-patternable ionogels:
tuning of conductivity and mechanical stability of 3D
microstructures," vol. 22, no. 21, pp. 10552-10559, 2012.
Ouyang et al., "High-conductivity poly (3, 4-ethylenedioxy-
thiophene): poly (styrene sulfonate) film and its applica-
tion in polymer optoelectronic devices," vol. 15, no. 2, pp.
203-208, 2005.
Piro et al., "A glucose biosensor based on modified-enzyme
incorporated within electropolymerised poly (3, 4-ethyl-
enedioxythiophene)(PEDT) films," J. Electroanal. Chem.
vol. 512, no. 1-2, pp. 101-109, 2001.
Qu et al., "Stiffness, strength and adhesion characterization
of electrochemically deposited conjugated polymer films,
" vol. 31, pp. 114-121, 2016.
Reetz, Adv. Mater. 1997, 9, 943.
Sakellari et al., "Diffusion-assisted high-resolution direct
femtosecond laser writing," vol. 6, no. 3, pp. 2302-2311,
2012.
Schell et al., "Single photon nanophotonics using NV cen-
ters in three-dimensional laser-written microstructures,"
in The European Conference on Lasers and Electro-
Optics, 2013, p. 71.
Senel & Nergiz, Curr. Appl. Phys. 2012, 12, 1118.
Setti et al., Biosens. Bioelectron. 2005, 20, 2019.
Sheldon, Adv. Synth. Catal. 2007, 349, 1289.
Shukla et al., "Subwavelength direct laser patterning of
conductive gold nanostructures by simultaneous photo-
polymerization and photoreduction," vol. 5, no. 3, pp.
1947-1957, 2011.
Soares et al., J. Mol. Catal., B Enzym. 2006, 39, 69.
Spangenberg et al., "Recent advances in two-photon stereo-
lithography," pp. 35-63, 2013.
Staudinger et al., "Development of electrically conductive
microstructures based on polymer/CNT nanocomposites
via two-photon polymerization," vol. 179, pp. 48-55,
2017.
Stillman et al., Polym. Chem. 2020, 11, 568.
Sun et al., Electrochim. Acta, 2007, 52, 7352.
Sun et al., "Multicolor polymer nanocomposites: in situ
synthesis and fabrication of 3D microstructures," vol. 20,
no. 5, pp. 914-919, 2008.

Takenaga et al., "Fabrication of biocompatible lab-on-chip devices for biomedical applications by means of a 3D-printing process," vol. 212, no. 6, pp. 1347-1352, 2015.

Tang et al., *Anal. Biochem.* 2004, 331, 89.

Tao et al., "Carbon nanotube-doped electric hydrogels via ultrafast laser processing and loading conductive polymer," in 14*th National Conference on Laser Technology and Optoelectronics,* 2019a, vol. 11170, p. 111703U: International Society for Optics and Photonics.

Tao et al., "Nanostructured electrically conductive hydrogels obtained via ultrafast laser processing and self-assembly," vol. 11, no. 18, pp. 9176-9184, 2019b.

Terzaki et al., "3D conducting nanostructures fabricated using direct laser writing," vol. 1, no. 4, pp. 586-597, 2011.

Tiwari & Tiwari, *Pharm. Methods* 2010, 2, 25.

Tsen et al., *J. Phys. Condens. Matter.* 2007, 19, 472201.

Wang et al., "Glucose metabolic changes in nontumoral brain tissue of patients with brain tumor following radiotherapy: a preliminary study," vol. 20, no. 5, pp. 709-714, 1996.

Wang et al., "Polymer-enriched 3D graphene foams for biomedical applications," vol. 7, no. 15, pp. 8275-8283, 2015.

Whiting et al., "IDF diabetes atlas: global estimates of the prevalence of diabetes for 2011 and 2030," vol. 94, no. 3, pp. 311-321, 2011.

Wigle et al., *J. Biomed. Opt.* 2014, 19, 015008.

Xia et al., "Ferrofluids for fabrication of remotely controllable micro-nanomachines by two-photon polymerization," vol. 22, no. 29, pp. 3204-3207, 2010.

Xiong et al., "Laser-Directed Assembly of Aligned Carbon Nanotubes in Three Dimensions for Multifunctional Device Fabrication," vol. 28, no. 10, pp. 2002-2009, 2016.

Xue et al., *Electrochem. Commun.* 2006, 8, 1468.

Yang et al., *Electrochem. Commun.* 2006, 8, 665.

Yang et al., "High performance conducting polymer nanofiber biosensors for detection of biomolecules," *Adv. Mater. vol.* 26, no. 29, pp. 4954-4960, 2014.

Zeira et al., *Mol. Ther.* 2003, 8, 342.

Zhang et al., *Bioelectrochemistry* 2005, 67, 15.

Zhang et al., "Integrating valve-inspired design features into poly (ethylene glycol) hydrogel scaffolds for heart valve tissue engineering," vol. 14, pp. 11-21, 2015.

Zhang & Cicoira, *Adv. Mater.* 2017, 29, 1.

Zhao et al., "Modeling and characterization of carbon-based heterogeneous interconnects for 3-D ICs," in 2013 *IEEE Electrical Design of Advanced Packaging Systems Symposium (EDAPS),* 2013, pp. 154-157.

Zustiak & Leach, *Biomacromolecules* 2010, 11, 1348.

What is claimed is:

1. A two-photon polymerization (TPP) compatible photosensitive ink or resin, wherein said ink or resin comprises at least one organic semiconductor, crosslinker, photoinitiator, and solvent:

(a) wherein the at least one organic semiconductor is poly (3,4-ethylenedioxythiophene)-poly(styrenesulfonate) (PEDOT:PSS) present at 0.1%-0.5% wt, the crosslinker is polyethylene glycol diacrylate (PEGDA), and the solvent is DMSO present at 25%-35% wt; or (b) wherein the ink or resin comprises two organic semiconductions comprising poly (3,4-ethylenedioxythiophene)-poly(styrenesulfonate) (PEDOT:PSS) and multi-walled carbon nanotubes (MWCNTs).

2. The ink or resin of claim 1, wherein the ink or resin comprises two organic semiconductors comprising poly (3,4-ethylenedioxythiophene)-poly(styrenesulfonate) (PEDOT:PSS) and multi-walled carbon nanotubes (MWCNTs).

3. The ink or resin of claim 1, wherein the photoinitiator is ethyl (2,4,6-trimethylbenzoyl) phenylphosphinate (T-POL).

4. The ink or resin of claim 1, wherein the solvent is dimethyl sulfoxide (DMSO).

5. The ink or resin of claim 2, wherein the solvent for PEDOT:PSS is DMSO and the solvent for the MWCNTs is pentaerythritol tetrakis(3-mercaptopropionate) (PETMP).

6. The ink or resin of claim 1, wherein the ink or resin comprises one organic semiconductor and wherein the solvent is present at 25-45 wt %, the PEPDOT:PSS is present at 0.1-0.5 wt %, the crosslinker is present at 72.5-72.9 wt %, the solvent is DMSO present at 25%-35% wt, and the photoinitiator is present at 2 wt %.

7. The ink or resin of claim 5, wherein the PETMP is present at 18.75 wt %, DMSO is present at 24.7-24.9 wt %, the PEPDOT:PSS is present at 0.1-0.4 wt %, MWCNT is present at 0.05-0.15 wt %, the crosslinker is present at 54 wt %, and/or the photoinitiator is present at 1.95 wt %.

8. The ink or resin of claim 1, further comprising a biologically active agent and/or a chemical species.

9. The ink or resin of claim 8, wherein the biologically active agent a protein, a nucleic acid, a carbohydrate or a lipid.

10. The ink or resin of claim 8, wherein the bioactive agent is an extracellular protein, a growth factor, an enzyme, a neurotransmitter, a cell adhesive protein or peptide, or a glycosaminoglycan.

11. The ink or resin of claim 8, wherein one or more biologically active molecules is/are present at 1-300 $\mu$g ml$^{-1}$ and/or 100-4000 KU ml$^{-1}$ in the ink.

12. The ink or resin of claim 8, wherein the chemical species is an ion.

13. The ink or resin of claim 1, wherein the ink or resin is in the form of a homogenous liquid.

14. The ink or resin of claim 1, wherein the ink or resin is in the form of a solid.

15. A fabricated device composed of the ink or resin of claim 1.

16. The device of claim 15, wherein said device comprises a three-dimensional structure selected from a conductive filler, a semiconductive nanoparticle, or a magnetic particle.

17. The device of claim 1, wherein the device is a TPP-fabricated microdevice.

18. The device of claim 1, wherein the device is a micro/nanoelectronic, a battery, an optic element, a flexible electronic device, a printed circuit board, a chip-scale electronic, a chemical/biological sensor, a micro/nano electromechanical system, an organic bioelectronic, a neural interface, a neural recording and/or stimulation device, a wearable biosensor, a bioactuator, a soft robotic, a tissue engineering scaffold, or a bioprinted organ.

19. A method of detecting an analyte in sample or subject comprising contacting said sample or subject with a device coated with a two-photon polymerization (TPP) compatible photosensitive ink or resin, wherein said ink or resin comprises at least one organic semiconductor, crosslinker, photoinitiator, and solvent and a biological molecule that binds and/or reacts with said analyte to produce a detectable event.

* * * * *